US012446868B2

(12) United States Patent
O'Dea et al.

(10) Patent No.: US 12,446,868 B2
(45) Date of Patent: Oct. 21, 2025

(54) CLIP AND A METHOD FOR RELEASABLY SECURING TWO ELONGATED MEMBERS TOGETHER

(71) Applicant: Palliare Limited, Galway (IE)

(72) Inventors: John O'Dea, Bearna (IE); Hilary Elizabeth Barrett, Limerick (IE); Martin James Hamilton Bruggemann, County Laois (IE); Paul Maurice Cremin, Dublin (IE)

(73) Assignee: Palliare Limited, Galway (IE)

( * ) Notice: Subject to any disclaimer, the term of this patent is extended or adjusted under 35 U.S.C. 154(b) by 443 days.

(21) Appl. No.: 17/996,208

(22) PCT Filed: Apr. 14, 2021

(86) PCT No.: PCT/IE2021/000008

§ 371 (c)(1),
(2) Date: Oct. 13, 2022

(87) PCT Pub. No.: WO2021/209983

PCT Pub. Date: Oct. 21, 2021

(65) Prior Publication Data

US 2023/0190080 A1 Jun. 22, 2023

(30) Foreign Application Priority Data

Apr. 14, 2020 (IE) .................................. S2020/0061

(51) Int. Cl.
*A61B 1/00* (2006.01)
*A61B 17/00* (2006.01)

(52) U.S. Cl.
CPC ...... *A61B 17/00234* (2013.01); *A61B 1/0014* (2013.01); *A61B 1/00147* (2013.01);
(Continued)

(58) Field of Classification Search
CPC .............. A61B 1/0014; A61B 1/00147; A61B 2017/00296; A61B 17/00234
See application file for complete search history.

(56) References Cited

U.S. PATENT DOCUMENTS

D376,309 S 12/1996 Takai
D544,787 S 6/2007 Dash
(Continued)

FOREIGN PATENT DOCUMENTS

GB 9007809405-0004 4/2020
KR 301150188.0000 S 2/2022
(Continued)

OTHER PUBLICATIONS

Double Clip 2" x 2.5" diameter, Fresh Water Systems, [Post Date: unknown], [Site seen Apr. 20, 2022], Seen at URL: https://www.freshwatersystems.com/products/double-clip-2-x-2-5-diameter (Year: 2022).

(Continued)

*Primary Examiner* — Timothy J Neal
(74) *Attorney, Agent, or Firm* — Sughrue Mion, PLLC

(57) ABSTRACT

A clip assembly (42) for securing a tubular member (5) to an endoscope (3) comprises a plurality of clips (40) tethered together by a looped tether (41). Each clip (40) comprises a first channel (48) for engaging the endoscope (3) and a second channel (50) for engaging the tubular member (5). Each clip comprises a carrier element (45) and an adapter element (47) secured to the carrier element (45). The carrier element (45) comprises a body member (52) having a pair of first side members (54) extending therefrom defining the first channel (48), and a pair of engagement side members (67) defining an engagement channel (69). The adapter element comprises an arcuate element (80) engaged in the engagement channel (69) for defining the second channel (50). A covering element (95) comprising a pair of end
(Continued)

Figure 1:
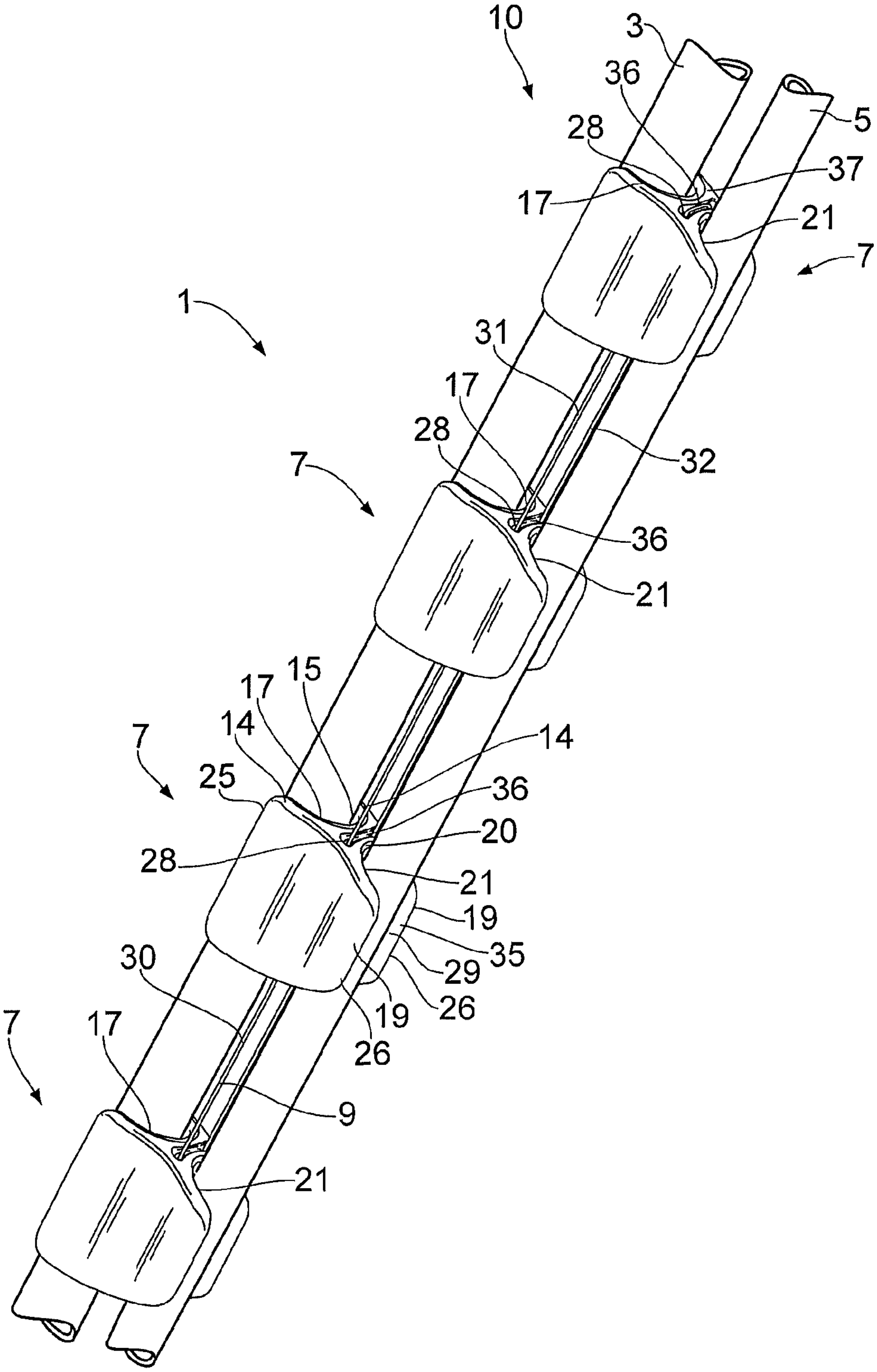

panels (91) extending from the arcuate element (80) cover ends (61) of the carrier element (45). Lower portions (96) of the covering element (95) are engageable with a snap-fit action with corresponding receiving recesses (92) in the carrier element (45) for securing the adapter element (47) to the carrier element (45).

20 Claims, 20 Drawing Sheets

(52) U.S. Cl.
CPC ............... *A61B 2017/00296* (2013.01); *A61B 2017/00862* (2013.01)

(56) References Cited

U.S. PATENT DOCUMENTS

| | | | |
|---|---|---|---|
| D563,551 S | 3/2008 | Schwelkert | |
| D575,143 S | 8/2008 | Kuo | |
| 7,566,300 B2 | 7/2009 | Devierre et al. | |
| D623,931 S | 9/2010 | Austro | |
| D647,788 S | 11/2011 | Weaver | |
| D655,407 S | 3/2012 | Adams | |
| D732,009 S | 6/2015 | Bak | |
| D734,451 S | 7/2015 | Guney | |
| D739,027 S | 9/2015 | Johnson | |
| D742,909 S | 11/2015 | Lee et al. | |
| D800,542 S | 10/2017 | O'Dea et al. | |
| 10,273,692 B1 | 4/2019 | Rush | |
| D852,354 S | 6/2019 | Wrangmark | |
| D870,881 S | 12/2019 | Mullani | |
| D877,323 S | 3/2020 | Reedy-Goss | |
| D890,924 S | 7/2020 | Godinez | |
| D895,408 S | 9/2020 | Heindl | |
| 10,758,706 B2 | 9/2020 | Monighetti | |
| D941,596 S | 1/2022 | Van Deursen | |
| D961,069 S | 8/2022 | O'Dea et al. | |
| 2005/0234297 A1* | 10/2005 | Devierre | A61B 1/00087 600/129 |
| 2016/0074628 A1* | 3/2016 | Smith | A61B 1/0014 604/174 |

FOREIGN PATENT DOCUMENTS

| | | |
|---|---|---|
| WO | 2016/092983 A1 | 6/2016 |
| WO | 2019/207546 A1 | 10/2019 |

OTHER PUBLICATIONS

Brickarms® U-Clip, Lego, eclipsegrafx.com, [Postdate unknown], [Siteseen Apr. 20, 2022], Seen at URL: https://www.eclipsegrafx.com/products/u-clip-black?variant=36864651493527 (Year: 2022).

International Search Report for PCT/IE2021/000008 dated Jul. 23, 2021.

Written Opinion for PCT/IE2021/000008 dated Jul. 23, 2021.

* cited by examiner

CLIP AND A METHOD FOR RELEASABLY SECURING TWO ELONGATED MEMBERS TOGETHER

CROSS REFERENCE TO RELATED APPLICATIONS

This application is a National Stage of International Application No. PCT/IE2021/000008 filed Apr. 14, 2021, claiming priority based on Ireland Patent Application No. S2020/0061 filed Apr. 14, 2020.

The present invention relates to a clip for securing two members together, and in particular, though not limited, to a clip for securing two elongated members together, for example, a tubular member to an endoscope or for securing two elongated instruments for use in a surgical or investigative procedure together. The invention also relates to a clip assembly comprising a plurality of the clips for securing two elongated members together, and the invention further relates to an assembly comprising the two elongated members secured together by either one of the clips, or by the clip assembly. The invention also relates to a method for securing two members together, and in particular, though not limited to a method for securing two elongated members together.

During investigative and surgical procedures, which typically are being carried out in a cavity of a human or animal body, and which require the use of an endoscope, whereby an endoscope is introduced into the body cavity, orally, nasally or rectally, it is regularly necessary to insert an elongated member, such as a tube or an instrument such as a surgical instrument and the like into the body cavity along with the endoscope. In such cases, the elongated member, typically is passed into the body cavity along with the endoscope, with the elongated member being located adjacent and extending along a side of the endoscope. It is also known to releasably clip such an elongated member to an endoscope prior to inserting the endoscope into the body cavity for retaining the elongated member in tight adjacent relationship with the endoscope. However, a problem with the use of such clips, is that during insertion and withdrawal of the endoscope to and from the body cavity, one or more of the clips may become detached from both the endoscope and also from the elongated member, and may remain in the body cavity or elsewhere in the body of a subject on completion of the procedure. Identifying the location of such detached clips and their subsequent removal from the body cavity or elsewhere in the body can be a significantly difficult task. This is therefore undesirable and there is therefore a need to address this problem.

A further disadvantage of such clips is that as the instruments, which are clipped together with such known clips, are being urged through one or more lumens, vessels or cavities to the cavity in which the procedure is to be carried out, the inner surface and the lining of such lumens, vessels and cavities may be injured or damaged. For example, the lining or inner surface of such lumens, vessels or cavities may be grazed, bruised or ruptured by corners, edges or projections of such clips. Indeed, such injuries, damage, grazing, bruising or rupturing of the inner surface or lining of the cavity in which the procedure is being carried out may also occur. This is clearly undesirable, and there is therefore a need to address this problem.

The present invention is directed towards providing a clip and clip assembly for securing a pair of members together, and in particular, for securing a pair of elongated members together which addresses at least one of the above discussed problems. The invention is also directed towards providing an assembly comprising a pair of members, and in particular, a pair of elongated members secured together by either the clip or the clip assembly which addresses at least one of the above discussed problems. Further, the invention is directed towards providing a method for securing a pair of members, and in particular, a pair of elongated members together which addresses at least one of the above discussed problems.

According to the invention there is provided a clip for releasably securing a pair of elongated members together, the clip comprising a body member, a pair of spaced apart first side members extending from the body member, the first side members defining a first channel and cooperating with each other for releasably gripping and retaining a first one of the members to be secured together in the first channel, a pair of second side members extending from the body member, the second side members defining a passageway for accommodating a second one of the members to be secured together therein.

In one embodiment of the invention the first channel and the passageway extend parallel to each other.

In another embodiment of the invention the second side members extend from the body member from a side opposite to a side of the body member from which the first side members extend.

Preferably, the first side members terminate in respective spaced apart first distal side edges, the first distal side edges defining a first open mouth to the first channel.

Advantageously, at least one of the first side members is biased towards the other one of the first side members for gripping the first member in the first channel, and is resiliently urgeable away from the said other one of the first side members for accommodating the first side member into the first channel. Preferably, each of the first side members is biased towards the other one of the first side members for gripping the first member in the first channel.

In one embodiment of the invention each of the first side members comprise a resilient material.

In another embodiment of the invention the first channel defines a longitudinally extending first central axis.

In another embodiment of the invention the first side members extend around the first central axis an angular distance greater than 180°. Preferably, the first side members extend around the first central axis an angular distance in the range of 220° to 290°. Advantageously, the first side members extend around the first central axis an angular distance of approximately 273°.

In one embodiment of the invention at least one of the first side members is of arcuate shape, and preferably, both of the first side members are of arcuate shape.

Advantageously, each first side member defines a concave surface facing towards the other one of the first side members. Preferably, the concave surfaces of the first side members define a part of the first channel, and advantageously, the body member defines a part of the first channel, and preferably, the part of the body member which defines a part of the first channel defines a concave surface.

In one embodiment of the invention the first channel is of partly circular transverse cross-section.

In another embodiment of the invention the passageway defines a longitudinally extending second central axis, the second central axis extending parallel to the first central axis.

Preferably, the second side members extend from the body member at spaced apart locations.

In one embodiment of the invention the second side members terminate in respective spaced apart second distal side edges to form the passageway as a second channel, the second distal side edges defining a second open mouth to the second channel.

In another embodiment of the invention the first and second open mouths face away from the first and second channels in opposite directions.

In another embodiment of the invention at least one of the second side members is biased towards the other one of the second side members for gripping the second member in the second channel, and is resiliently urgeable away from the said other one of the second side members for accommodating the second side member into the second channel. Preferably, each of the second side members is biased towards the other one of the second side members for gripping the second member in the second channel.

In another embodiment of the invention each of the second side members comprise a resilient material.

In one embodiment of the invention the second side members extend around the second central axis an angular distance greater than 180°. Preferably, the second side members extend around the second central axis an angular distance in the range of 200° to 270°. Advantageously, the second side members extend around the second central axis an angular distance of approximately 250°.

In one embodiment of the invention at least one of the second side members is of arcuate shape, and preferably, both of the second side members are of arcuate shape.

Advantageously, each second side member defines a concave surface facing towards the other one of the second side members. Preferably, the concave surfaces of the second side members define a part of the second channel, and advantageously, the body member defines a part of the second channel, and preferably, the part of the body member which defines a part of the second channel defines a concave surface.

In one embodiment of the invention the second channel is of partly circular transverse cross-section.

In another embodiment of the invention the second side members join each other adjacent respective distal ends thereof to form the passageway as an engagement bore to accommodate the second one of the members therein.

In another embodiment of the invention the engagement bore formed by the second side members is of substantially circular transverse cross-section.

In one embodiment of the invention the passageway is adapted to slideably engage the second one of the members therein. In an alternative embodiment of the invention the passageway is adapted to tightly engage the second one of the members.

Preferably, the body member comprises a resilient material.

In one embodiment of the invention the first and second side members are integrally formed with the body member in one piece. Preferably, the first and second side members are integrally formed with the body member in one piece by injection moulding.

In one embodiment of the invention the body member comprises a plastics material.

In one embodiment of the invention at least one tether accommodating aperture is provided in or on the body member for accommodating a tether therethrough for tethering the clip to at least one other clip. Preferably, the tether accommodating aperture defines a longitudinal central tether axis, the central tether axis extending substantially parallel to one of the first and second central axes. Advantageously, a pair of spaced apart tether accommodating apertures are provided in or on the body member, the central tether axes thereof extending parallel to each other.

In one embodiment of the invention the tether accommodating apertures of the pair thereof are configured to engage both legs of a looped tether. Preferably, each tether accommodating aperture comprises an elongated tether accommodating bore extending through the body member.

The invention also provides a clip assembly comprising a plurality of the clips according to the invention retained in series by a tether.

In one embodiment of the invention the tether is adapted to permit the clips to be spaced apart in series along the tether.

In another embodiment of the invention the tether comprises a loop, one leg of the loop passing through one of the tether accommodating apertures of the respective clips and the other leg of the loop passing through the other one of the tether accommodating apertures of the respective clips.

Preferably, the tether comprises an endless loop.

Further the invention provides an assembly comprising an elongated first member and an elongated second member releasably secured together by the clip according to the invention.

The invention also provides an assembly comprising an elongated first member and an elongated second member releasably secured together by a clip assembly according to the invention with the clips according to the invention of the clip assembly being spaced apart longitudinally along the first and second members.

In one embodiment of the invention the assembly comprises an instrument assembly, one of the first and second members comprising an endoscope, and the other one of the first and second members comprising one of a tubular member and an instrument.

Additionally, the invention provides a method for releasably securing an elongated first member and an elongated second member together, the method comprising releasably securing at least one of the clips according to the invention to the first member with the first member releasably secured in the first channel of the at least one clip, and locating the second member in the passageway of the at least one clip with the second member releasably located in the passageway.

In one embodiment of the invention the first and second members are secured by a plurality of the clips, the clips being located spaced apart longitudinally along the first and second members.

In another embodiment of the invention the method further comprises tethering the clips in series with a tether extending through at least one of the first tether accommodating apertures of the respective clips.

Preferably, the tether comprises a loop tether, with the legs of the loop tether extending through the respective tether accommodating apertures of each of the clips in series thereof.

Advantageously, the free ends of the tether are secured together in order to form an endless loop.

In one embodiment of the invention the clips are tethered by the tether prior to being engaged with the first and second members.

In another embodiment of the invention the first member comprises an endoscope, and the second member comprises one of a tube, a tubular member and a medical or surgical instrument.

The invention also provides a clip for securing a pair of members together, the clip comprising a carrier element defining a first channel for engaging a first one of the pair of the members to be secured together, and a first passageway for accommodating a second one of the pair of the members to be secured together therein or an adapter element for reducing the transverse cross-section of the first passageway to define a second passageway therethrough of reduced transverse cross-section to that of the first passageway for engaging the second member, and a covering element configured for covering at least a portion of an external surface of the carrier element.

In one embodiment of the invention the first channel is configured for releasably engaging the first one of the members to be secured together.

Preferably, the transverse cross-section of the first channel is less than the transverse cross-section of the first member.

In another embodiment of the invention the carrier element comprises a body member, and the first channel is defined by a pair of spaced apart first side members extending from the body member.

Preferably, each first side member terminates in a first distal side edge, and the first distal side edges of the respective first side members define an open mouth to the first channel.

In one embodiment of the invention the first distal side edges of the first side members define first lead-ins to the first channel for accommodating entry of the first member into the first channel.

In one embodiment of the invention at least one of the first side members is biased towards the other one of the first side members for gripping the first member in the first channel, and is resiliently urgeable away from the said other one of the first side members for accommodating the first side member into the first channel. Preferably, each of the first side members is biased towards the other one of the first side members for gripping the first member in the first channel.

Advantageously, each of the first side members comprise a resilient material.

In one embodiment of the invention at least one of the first side members defines a concave surface facing towards the other one of the first side members. Preferably, both of the first side members define respective concave surfaces facing each other.

In another embodiment of the invention the first channel is of partly circular transverse cross-section.

In one embodiment of the invention the body member defines a part of the first channel. Preferably, the part of the body member defining the part of the first channel defines a concave surface.

In one embodiment of the invention the first channel defines a longitudinally extending first central axis.

In another embodiment of the invention the first channel extends around the first central axis between the first distal side edges of the first side members an angular distance of at least 180°. Preferably, the first channel extends around the first central axis between the first distal edges of the first side members an angular distance in the range of 200° to 270°. Advantageously, the first channel extends around the first central axis between the first distal edges of the first side members an angular distance in the range of 230° to 260°. Ideally, the first channel extends around the first central axis between the first distal edges of the first side members an angular distance of approximately 250°.

In another embodiment of the invention the first passageway defines a longitudinally extending first passageway central axis, the first passageway central axis extending substantially parallel to the first central axis of the first channel.

In another embodiment of the invention the first passageway is defined by a pair of engagement side members extending from the body member.

In one embodiment of the invention the engagement side members and the first side members extend from the body member in respective opposite directions therefrom.

In another embodiment of the invention the engagement side members extend from the body member at spaced apart locations.

In another embodiment of the invention engagement side members terminate in respective distal side edges spaced apart from each other, and define the first passageway as an engagement channel, the distal side edges of the respective engagement side members define an open mouth to the engagement channel.

In another embodiment of the invention the distal side edges of the engagement side members define second lead-ins to the engagement channel or the second channel for accommodating the second member into the engagement channel or the second channel.

In one embodiment of the invention at least one of the engagement side members is biased towards the other one of the engagement side members for gripping the one of the second member and the adapter element in the engagement channel, and is resiliently urgeable away from the said other one of the engagement side members for accommodating the one of the second member and the adapter element into the engagement channel. Preferably, each of the engagement side members is biased towards the other one of the engagement side members for gripping the one of the second member and the adapter element in the engagement channel. Preferably, each of the engagement side members comprise a resilient material.

In one embodiment of the invention at least one of the engagement side members defines a concave surface facing towards the other one of the engagement side members. Preferably, each of the engagement side members define a concave surface facing towards the other one of the concave surfaces of the other engagement side member.

In one embodiment of the invention the body member defines a part of the engagement channel. Preferably, the part of the body member defining the part of the engagement channel defines a concave surface.

In one embodiment of the invention the engagement channel is of partly circular transverse cross-section.

In another embodiment of the invention the engagement channel extends around the first passageway central axis between the distal side edges of the engagement side members an angular distance of at least 180°. Preferably, the engagement channel extends around the first passageway central axis between the distal side edges of the engagement side members an angular distance in the range of 200° to 300°. Advantageously, the engagement channel extends around the first passageway central axis between the distal side edges of the engagement side members an angular distance in the range of 220° to 290°. Ideally, the engagement channel extends around the first passageway central axis between the distal side edges of the engagement side members an angular distance of approximately 273°.

In another embodiment of the invention the engagement side members join each other adjacent respective distal ends thereof to form the first passageway as an engagement bore for accommodating the one of the second member and the adapter therein.

In one embodiment of the invention the engagement bore is of substantially circular transverse cross-section.

In one embodiment of the invention the first passageway is adapted to slideably engage the second one of the members. Alternatively, the first passageway is adapted to tightly engage the second one of the members.

In one embodiment of the invention at least one tether accommodating aperture is provided in or adjacent the carrier element for accommodating a tether therethrough.

In another embodiment of the invention the tether accommodating aperture defines a longitudinally extending central tether axis extending substantially parallel to one of the first central axis and the first passageway central axis. Preferably, the tether accommodating aperture extends through the body member. Advantageously, a pair of spaced apart tether accommodating apertures are provided in the carrier element.

Preferably, each tether accommodating aperture comprises an elongated tether accommodating bore extending through the carrier element.

In another embodiment of the invention the body member, the first side members and the engagement side members of the carrier member are integrally formed in one piece.

Preferably, the body member, the first side members and the engagement side members of the carrier member are integrally formed in one piece of a plastics material.

In one embodiment of the invention the carrier element is formed by injection moulding.

In another embodiment of the invention the carrier element comprises a resilient material.

In one embodiment of the invention the clip comprises the adapter element, the adapter element being engageable with the carrier element.

In another embodiment of the invention the adapter element is engageable with the first passageway for defining the second passageway for engaging the second member.

In one embodiment of the invention the second passageway defined by the adapter element defines a second central axis.

In another embodiment of the invention the second central axis coincides with the first passageway central axis.

In another embodiment of the invention the adapter element comprises an engagement portion engageable with the first passageway.

In one embodiment of the invention the engagement portion of the adapter element comprises an arcuate element having an inner surface defining the second passageway as a second channel for engaging the second member, and an outer surface defining the first passageway and being engageable in the first passageway.

In another embodiment of the invention the arcuate element of the adapter element terminates in a pair of spaced apart opposite longitudinally extending second distal side edges, the opposite second distal side edges of the arcuate element defining an elongated second open mouth to the second channel for accommodating the second member therethrough.

In another embodiment of the invention the arcuate element of the adapter element extends around the second central axis between the second distal side edges an angular distance greater than 180°.

Preferably, the arcuate element of the adapter element extends around the second central axis between the second distal side edges an angular distance in the range of 200° to 300°. Advantageously, the arcuate element of the adapter element extends around the second central axis between the second distal side edges an angular distance in the range of 220° to 295°. Ideally, the arcuate element of the adapter element extends around the second central axis between the second distal side edges an angular distance in the range of 273° to 292°.

In one embodiment of the invention the second channel is of partly circular transverse cross-section.

In another embodiment of the invention the transverse cross-section of the second channel is less than the transverse cross-section of the engagement channel.

In one embodiment of the invention at least one of the second distal side edges of the arcuate element is biased towards the other one of the second distal side edges for gripping the second member in the second channel, and is resiliently urgeable away from the said other one of the second distal side edges for accommodating the second member into the second channel. Preferably, the second distal side edges of the arcuate element are biased towards each other for gripping the second member in the second channel.

In one embodiment of the invention the arcuate element of the adapter element comprises a resilient material.

In one embodiment of the invention the engagement portion of the adapter element defines the second passageway as a bore extending therethrough for accommodating the second member therethrough.

In another embodiment of the invention the second passageway is adapted to slideably engage the second one of the members. In an alternative embodiment of the invention the second passageway is adapted to tightly engage the second one of the members.

In one embodiment of the invention the adapter element comprises the covering element for covering a part of the outer surface of the carrier element.

In another embodiment of the invention the covering element extends from the engagement portion of the adapter element.

In another embodiment of the invention the covering element comprises end covering members extending from the engagement portion of the adapter element adjacent respective opposite ends thereof. Preferably, the end covering members extend from the engagement portion of the adapter element from respective opposite ends thereof.

In one embodiment of the invention the covering element extends to locations adjacent the first distal side edges of the first side members of the carrier element.

In another embodiment of the invention a securing means is provided for securing the covering element to the carrier element.

In one embodiment of the invention the securing means of the adapter element is adapted to releasably engage the carrier element. In an alternative embodiment of the invention the securing means of the adapter element is adapted to non-releasably engage the carrier element.

In one embodiment of the invention the securing means of the adapter element is adapted to engage the carrier element with a snap-fit action.

Preferably, the securing means is adapted to engage the carrier element adjacent the first side members thereof.

In another embodiment of the invention the securing means comprises a pair of elongated securing members adapted to engage and extend along the respective first side members adjacent the first distal side edges thereof.

Preferably, the securing members extend between the end covering members of the covering element.

Advantageously, the securing members extend from distal portions of the end covering members.

Preferably, the end covering members of the covering element comprise end panels configured to cover opposite end surfaces defined by the carrier element.

In one embodiment of the invention the covering element comprises side covering members adapted to cover respective side surfaces defined by the carrier element.

In another embodiment of the invention the side covering members extend from opposite sides of the engagement portion of the adapter element.

Preferably, the side covering members extends from the distal side edges of the arcuate element, and define with respective portions of the arcuate element respective engagement recesses for accommodating the engagement side members of the carrier element therein.

In one embodiment of the invention each side covering element comprises a side panel extending between the respective end panels of the covering element.

In another embodiment of the invention the side panels extend to and terminate in the securing means.

In one embodiment of the invention the covering element is integrally formed with the engagement portion of the adapter element in one piece.

In one embodiment of the invention the material of the adapter element is of a hardness value less than the hardness value of the material of the carrier element.

In another embodiment of the invention the material of the adapter element is a softer material than the material of the carrier element.

In one embodiment of the invention the covering element is integrally formed with the engagement portion of the adapter element, and advantageously, is integrally formed with the engagement portion of the adapter element by injection moulding.

In one embodiment of the invention the adapter element comprises a resilient material.

In one embodiment of the invention the resilience of the material of the adapter element is such as to require a lesser force to deform the material of the adapter element, than the force required to deform the resilient material of the carrier element.

In another embodiment of the invention at least one tether accommodating aperture is provided in or on the adapter element, the at least one tether accommodating aperture being aligned with a corresponding one of the tether accommodating apertures in the carrier element.

In one embodiment of the invention a pair of spaced apart tether accommodating elements are provided in each of the end covering members, each pair of the tether accommodating apertures being aligned with the corresponding pair of tether accommodating apertures extending through the carrier element.

In another embodiment of the invention a plurality of adapter elements are provided, the adapter elements defining second passageways of respective different transverse cross-sections.

In one embodiment of the invention the tether accommodating apertures of the pair thereof are configured to engage both legs of a looped tether.

The invention also provides a clip assembly comprising a plurality of the clips according to the invention retained in series by a tether.

Preferably, the tether is adapted to permit the clips to be spaced apart in series along the tether. Advantageously, the tether is provided in the form of a loop, one leg of the loop passing through one of the tether accommodating apertures of the respective clips and the other leg of the loop passing through the other one of the tether accommodating apertures of the respective clips.

Preferably, the tether is provided in the form of an endless loop.

Further the invention provides an assembly comprising an elongated first member and an elongated second member secured together by at least one of the clips according to the invention.

Further the invention provides an assembly comprising an elongated first member and an elongated second member secured together by a clip assembly according to the invention with the clips being spaced apart longitudinally along the first and second members.

In one embodiment of the invention the assembly comprises an instrument assembly, the first member comprising an endoscope, and the second member comprising one of a tube, a tubular member and a medical or surgical instrument.

In another embodiment of the invention the assembly comprises a surgical instrument assembly.

The invention also provides a method for producing the clip according to the invention wherein the method comprises forming the carrier element and forming the adapter element and assembling the adapter element to the carrier element.

The invention also provides a method for producing a clip according to the invention, the method comprising forming one of the carrier element and the adapter element, and forming the other one of the carrier element and the adapter element within or around the already formed one of the carrier element and the adapter element.

In one embodiment of the invention the clip is formed by insert moulding with the already formed one of the carrier element and the adapter element being placed in a mould cavity of a moulding die and the other one of the carrier element and the adapter element being formed in or around the formed one of the carrier element and the adapter element.

Further the invention provides a method for releasably securing an elongated first member and an elongated second member together, the method comprising releasably locating at least one clip according to the invention on the first and second members with the first member releasably secured in the first channel, and the second member releasably located in the one of the first and second passageways.

Additionally the invention provides a method for releasably securing an elongated first member and an elongated second member together, the method comprising releasably locating a plurality of the clips according to the invention at spaced apart intervals along the first and second members with the first member releasably secured in the first channels of the clips, and the second member releasably located in the one of the first and second passageways of the clips In one embodiment of the invention the method further comprises tethering the clips in series with a tether extending through at least one of the tether accommodating apertures of the respective clips.

In another embodiment of the invention the tether comprises a loop tether, with the legs of the loop tether extending through the respective tether accommodating apertures of each of the clips in series.

In another embodiment of the invention the free ends of the tether are secured together to form an endless loop.

Preferably, the clips are tethered by the tether prior to being engaged with the first and second members.

In one embodiment of the invention the first member comprises an endoscope, and the second member comprises one of a tube, a tubular member and a medical or surgical instrument.

The advantages of the invention are many. A particular important advantage of the invention is that it provides a relatively simple construction of a clip which is readily suitable for securing one elongated member to another elongated member. A particularly important advantage of the invention is achieved when a plurality of the clips are tethered together as a clip assembly, in that a series of the tethered clips may be used for securing one elongated member to another elongated member, whereby the elongated members are secured together at spaced apart intervals along a length of the two members. By virtue of the fact that the clips of the clip assembly are tethered together, should one or more of the clips become detached from both of the elongated members, so long as at least one of the clips remain secured to one of the two elongated members, there is no danger of the disengaged clip or clips not being retrieved on withdrawal of the elongated members, for example, from a body cavity. Thus, where one of the elongated members is an instrument for entering into a body cavity of a human or animal subject, such as an endoscope, and the other is, for example, a tube for delivering insufflating gas to the cavity in which an investigative or surgical procedure is to be carried out, there is no danger of any of the clips, which may have become disengaged from both of the instruments which are secured together by the clip assembly, remaining in the cavity or any other part of the human or animal subject on withdrawal of the instruments on completion of the procedure.

Another important advantage of the invention is achieved when each clip is provided of two materials of different resilience. Where the carrier element of each clip is provided of a material of resilience which requires a greater force to deform the material than the material of the adapter element, and particularly, where the material of the adapter element is more yielding, elastic and softer than the material of the carrier element, the more yielding, elastic and softer material of the adapter element avoids any danger of grazing, bruising, rupturing or otherwise injuring or damaging of the inner surface or the inner lining of a lumen, vessel or cavity through which the instruments, which are secured together by one or more of the clips are being urged. By providing the adapter element to be of the more yielding, elastic and softer material, and particularly, by providing the covering element of the adapter element to be of such a more yielding, elastic and softer material whereby the covering element covers the opposite ends of the carrier element and the edges of the carrier element, there is little or no risk of any such grazing, bruising, rupturing or otherwise injuring or damaging the inner surface or the inner lining of a lumen, vessel or cavity in which the clips are located or are being urged therethrough. By providing the covering element of the adapter element to cover substantially the entire outer surface area of the carrier element, this advantage is further enhanced.

A further advantage of the invention is achieved when a number of the clips are provided with second passageways or second channels of respective different diameters and/or respective different transverse cross-sections, since a clip with the appropriately sized and/or shaped second passageway or second channel may be selected to suit the cross-section of the second member which is being attached to the first member.

Similar advantages to those achieved by the clip and the clip assembly according to the invention are achievable from the methods according to the invention.

Figure 2:
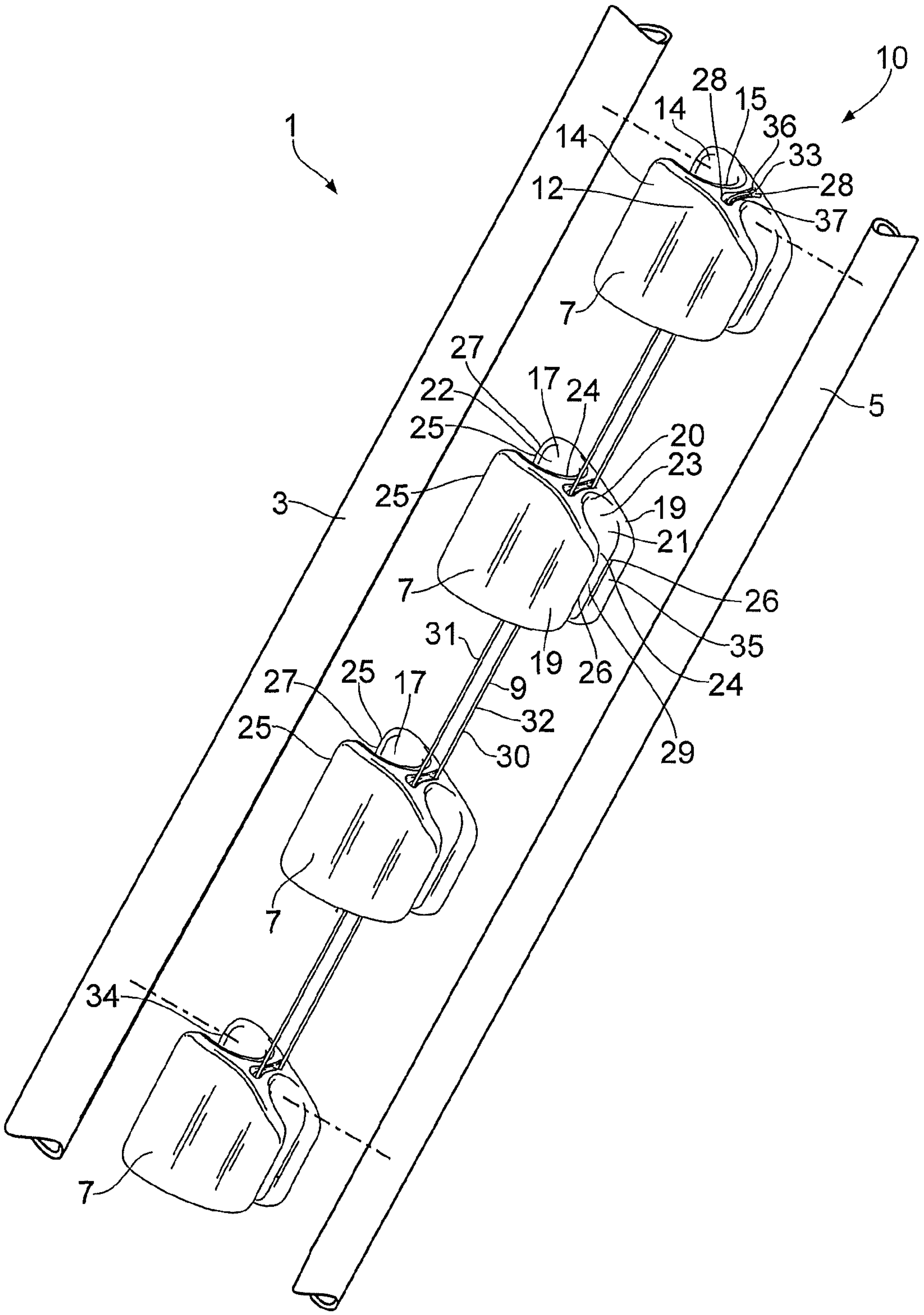
Figure 3:
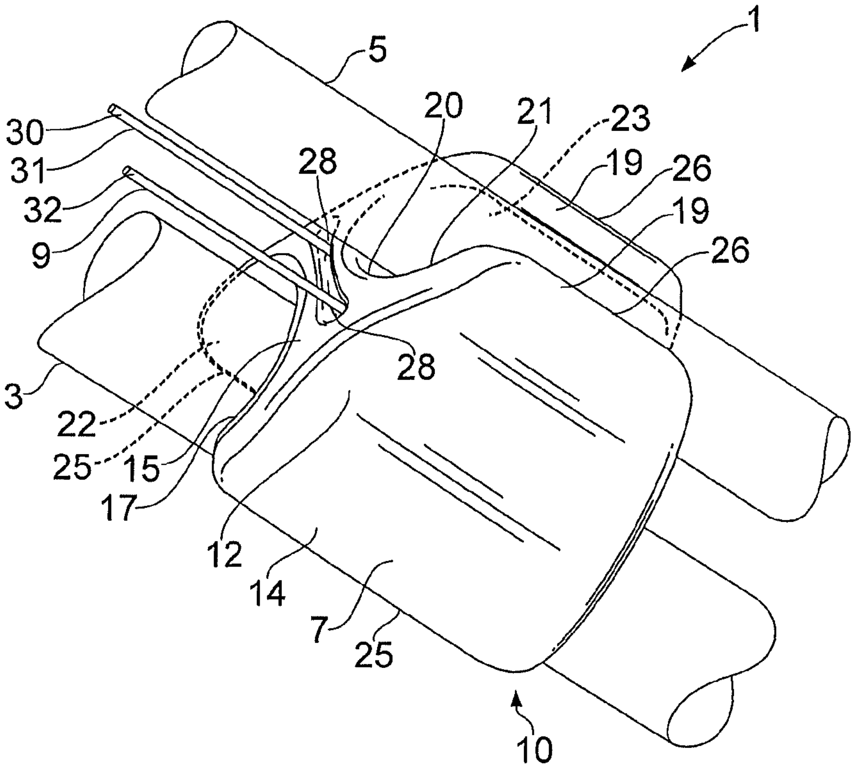
Figure 4:
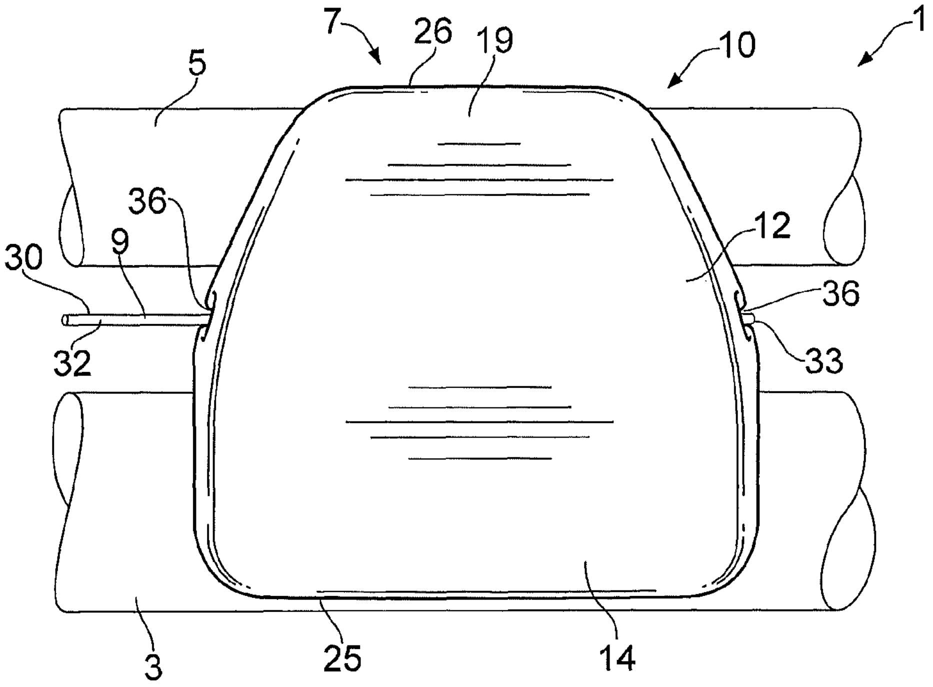
Figure 8:
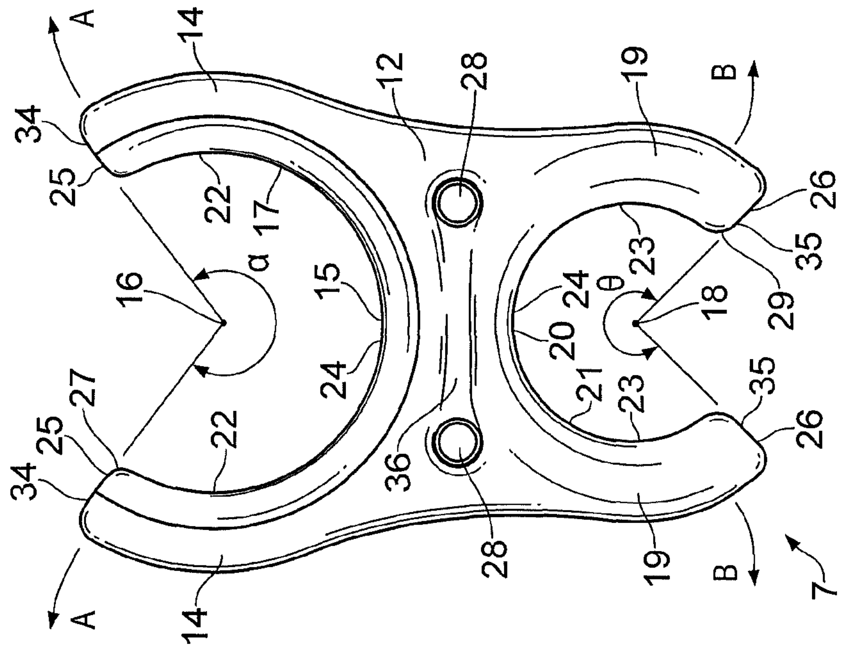
Figure 5:
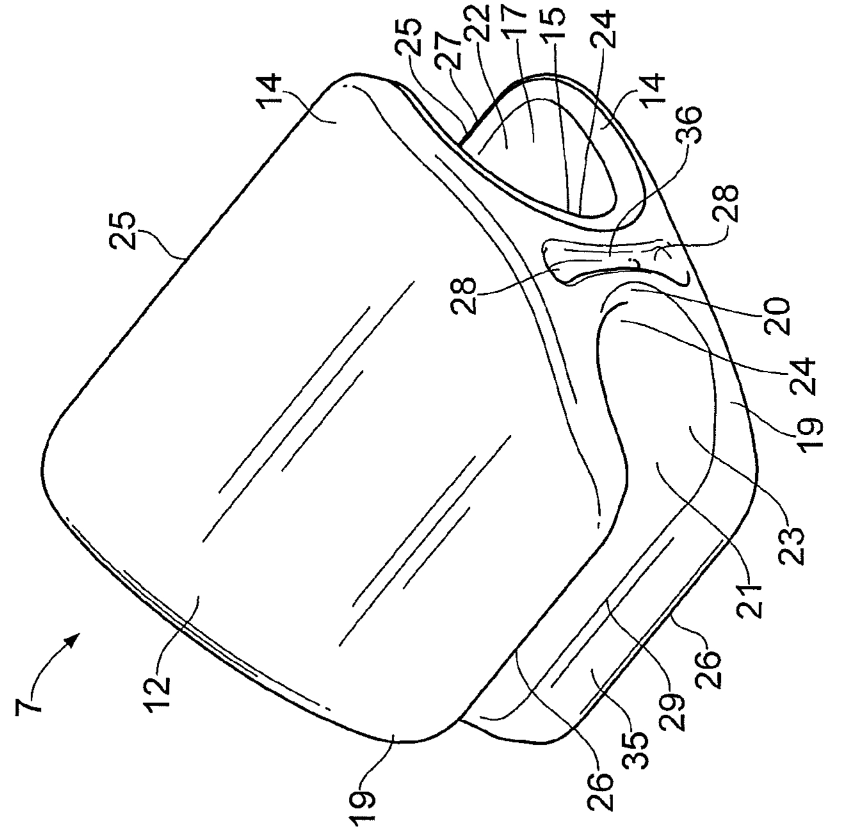
Figure 6:
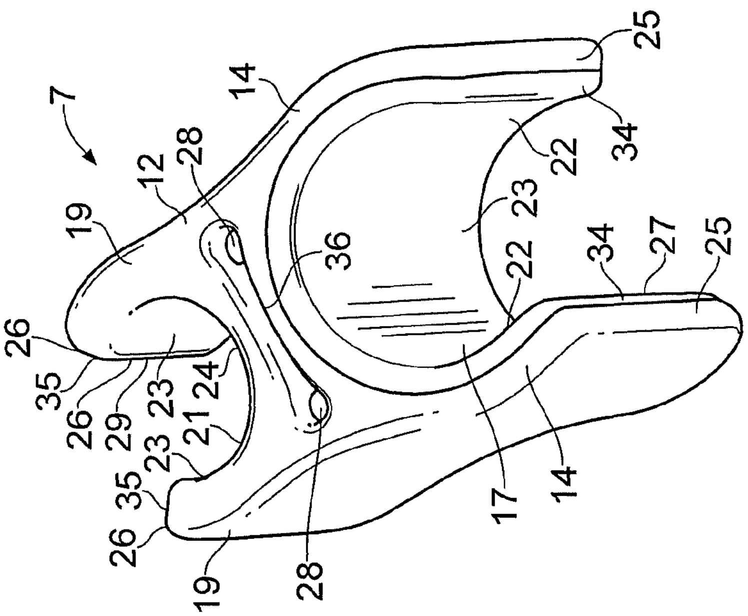
Figure 7:
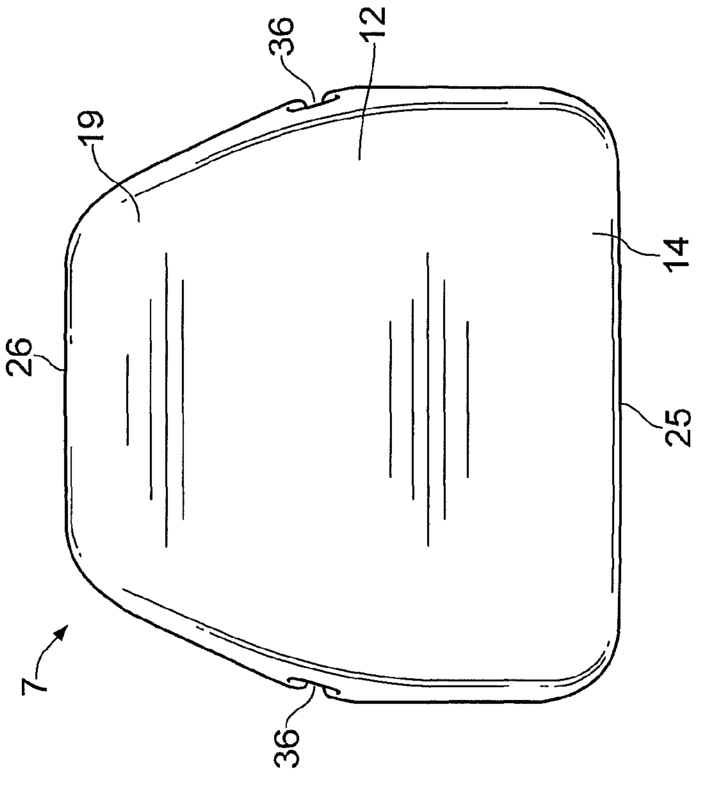
Figure 9:
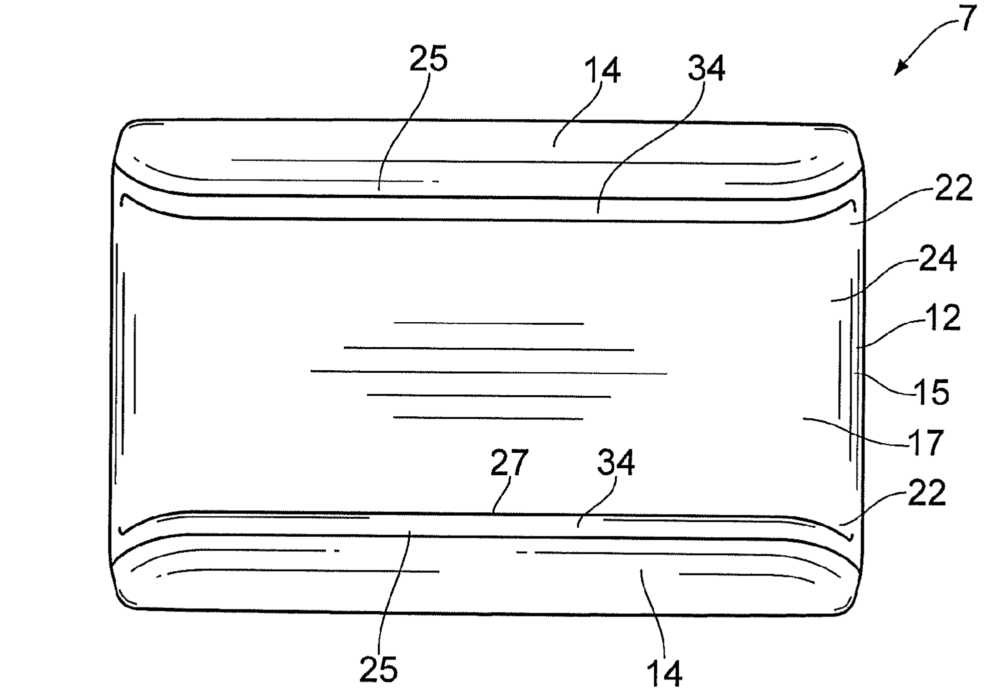
Figure 10:
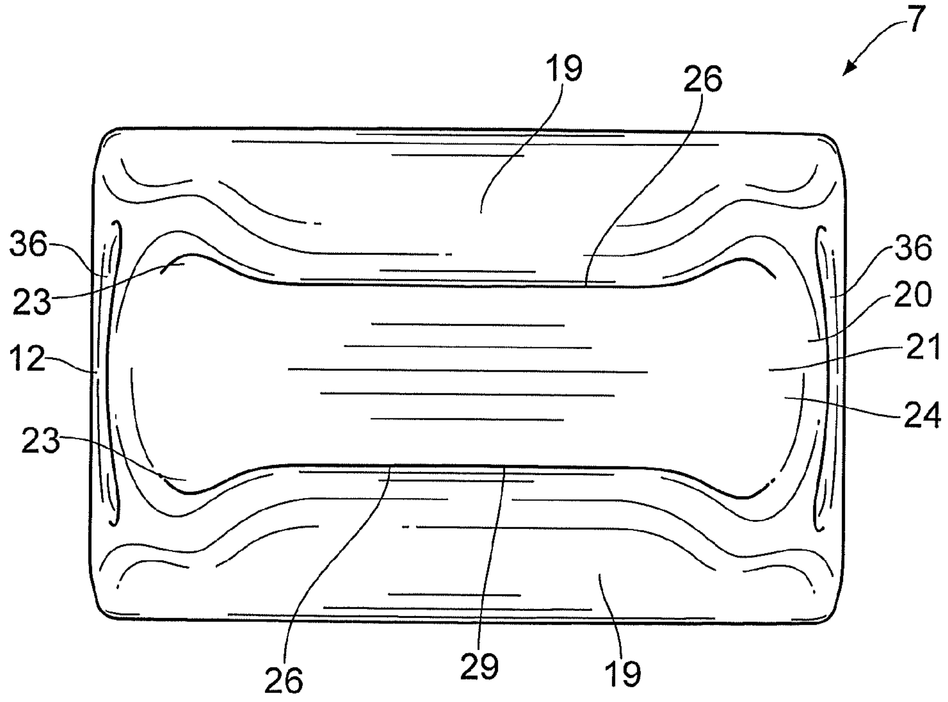
Figure 11:
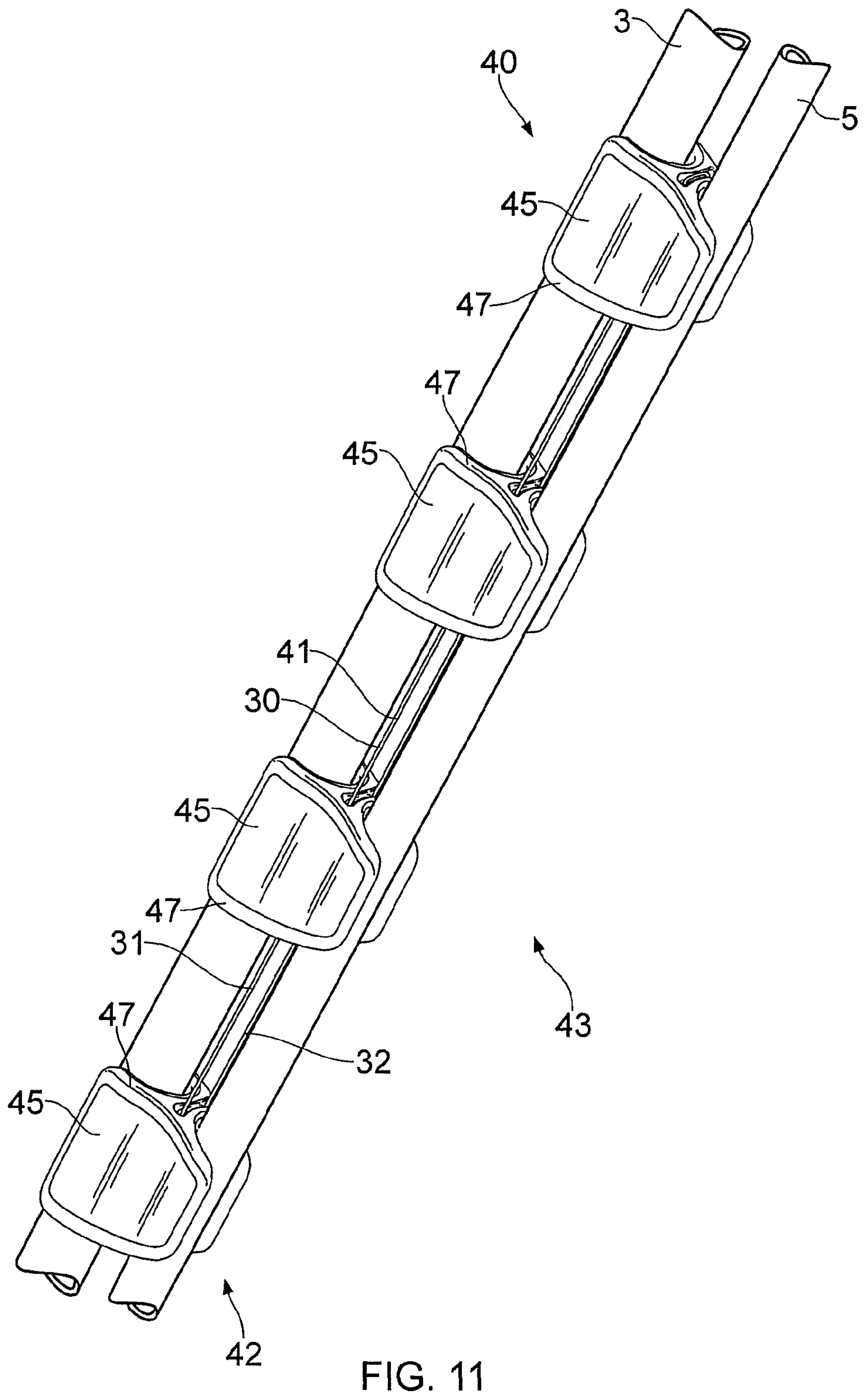
Figure 20:
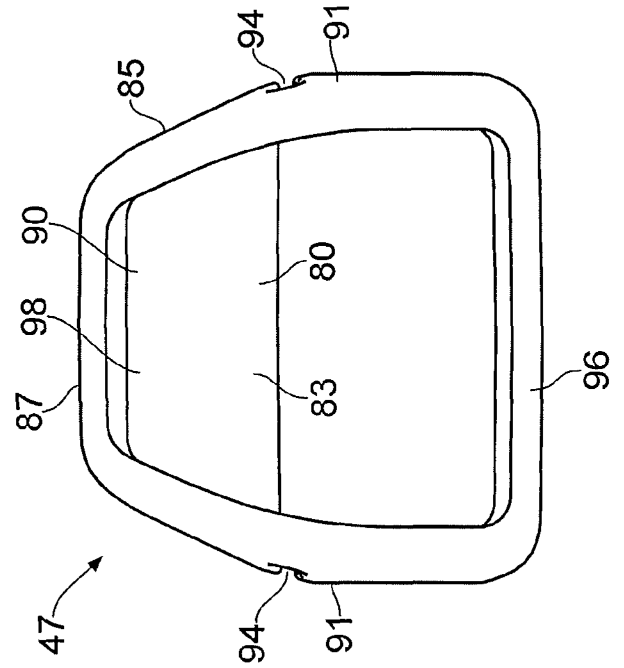
Figure 12:
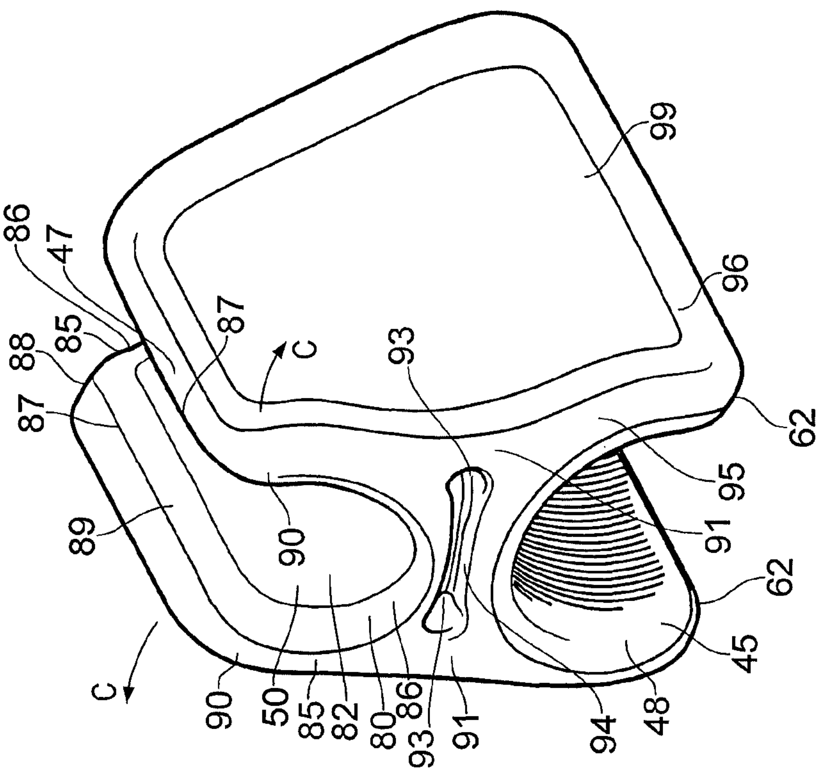
Figure 13:
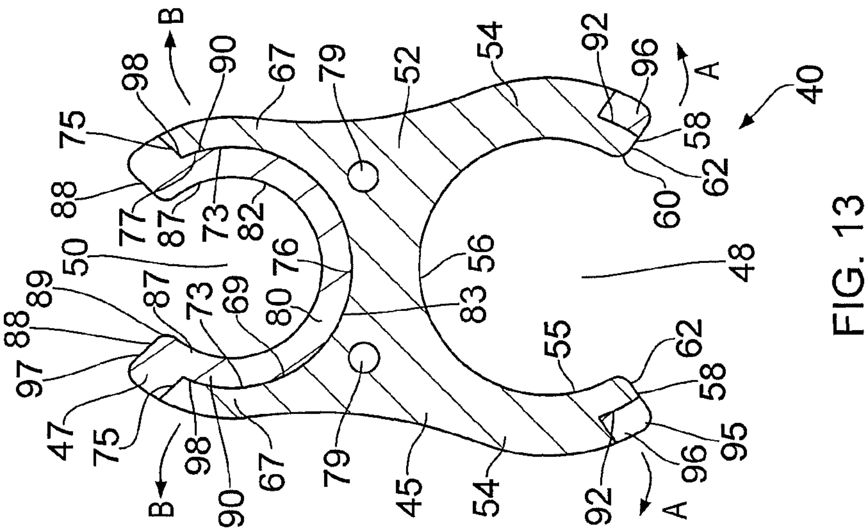
Figure 14:
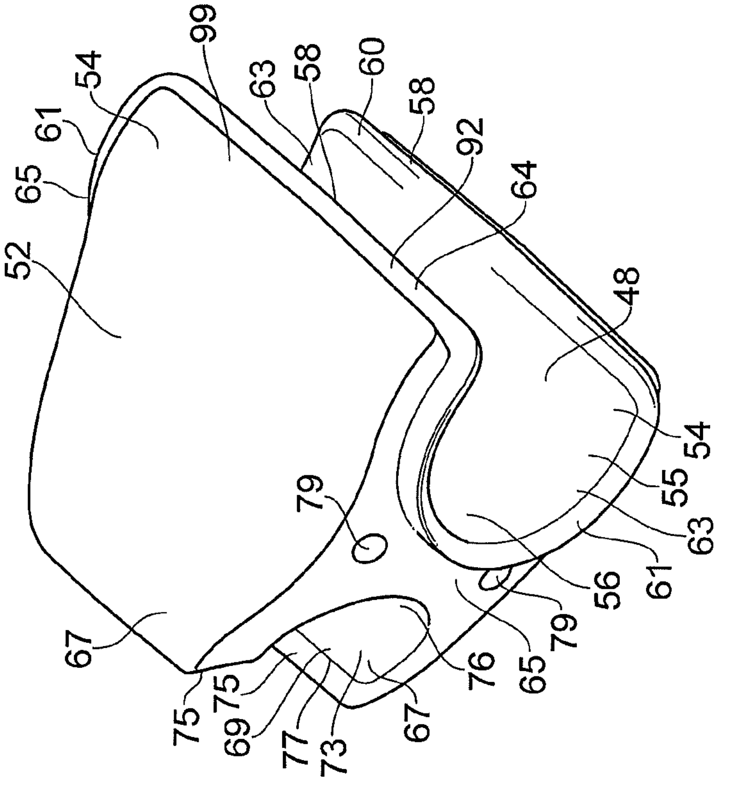
Figure 15:
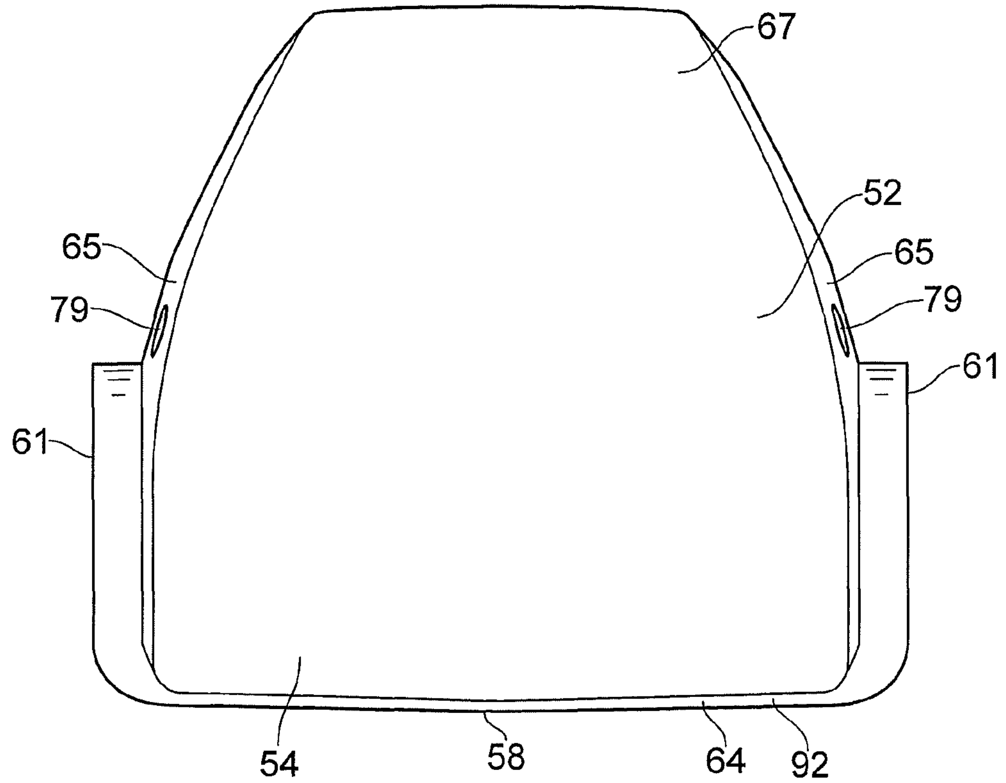
Figure 18:
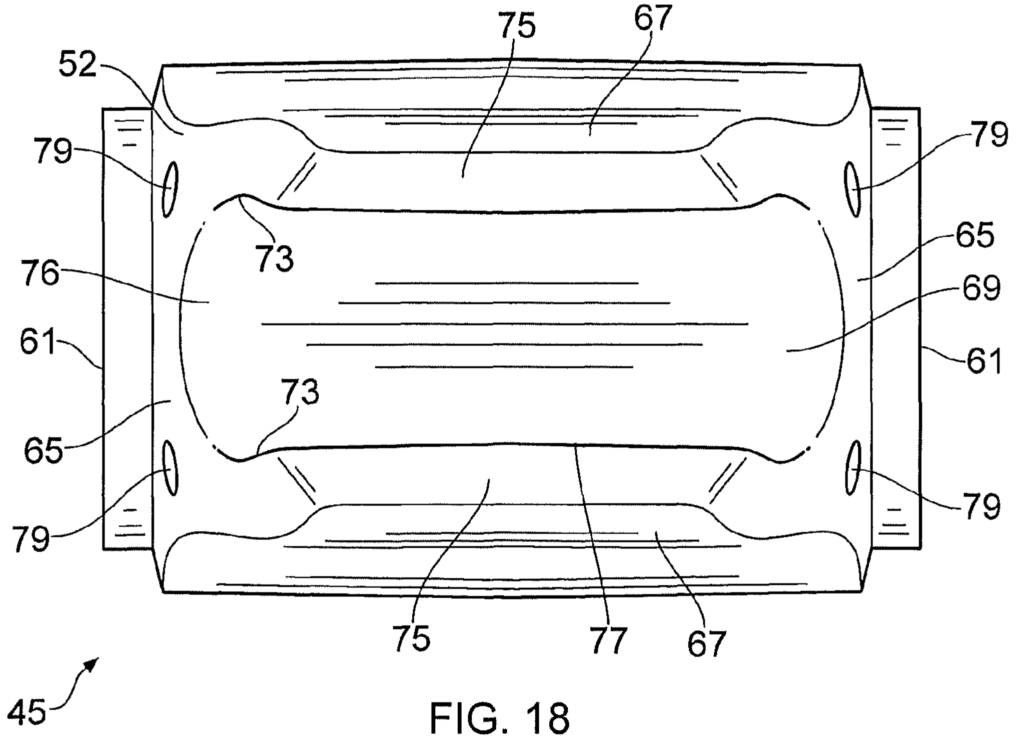
Figure 16:
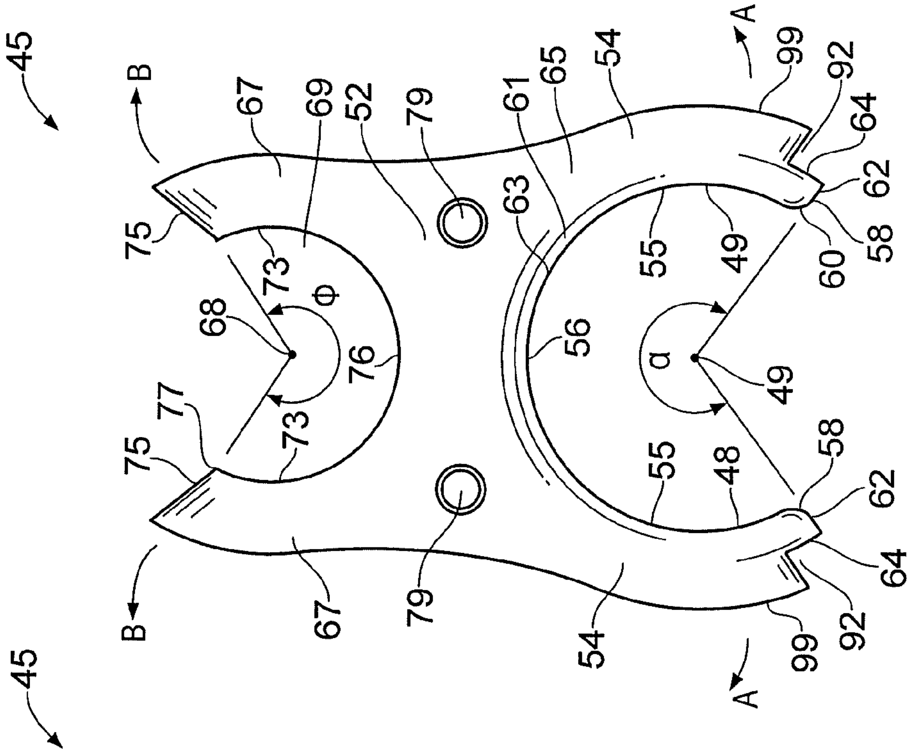
Figure 17:
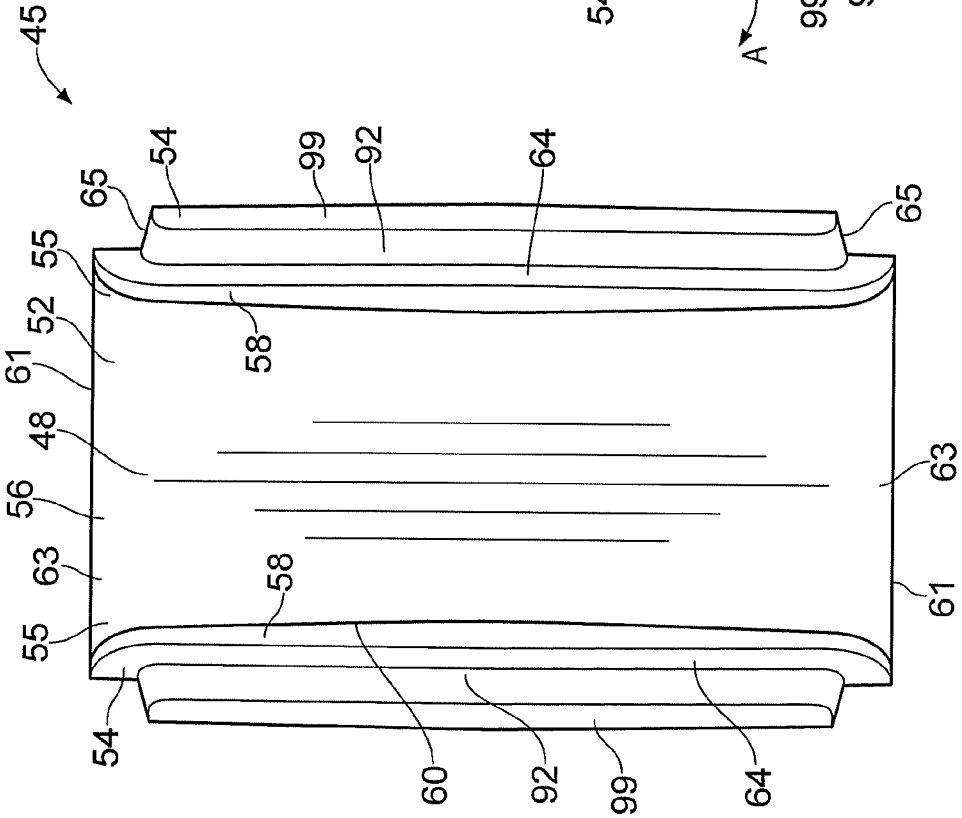
Figure 30:
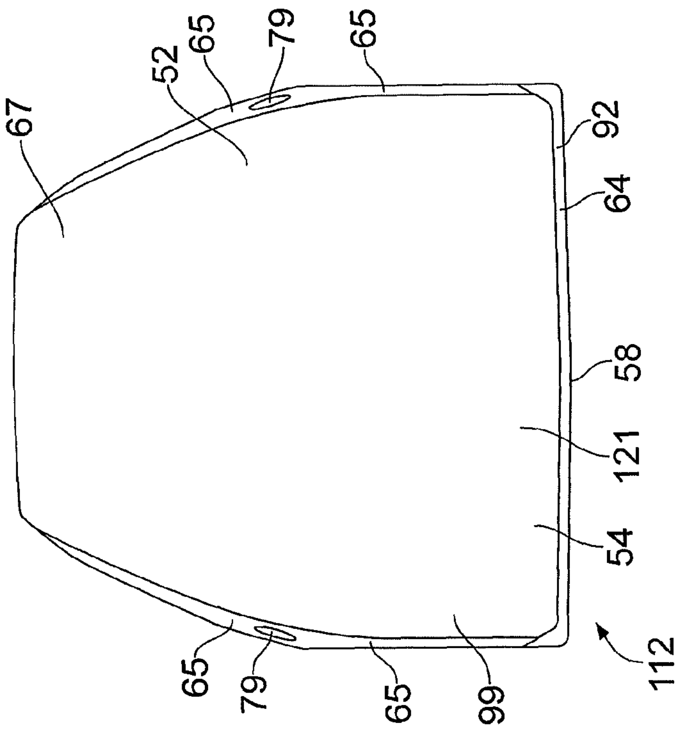
Figure 19:
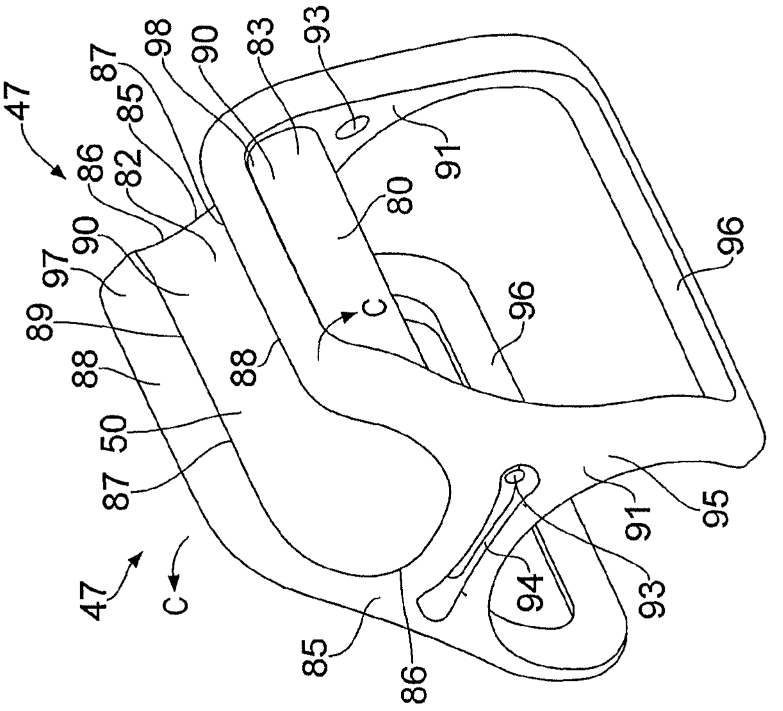
Figure 22:
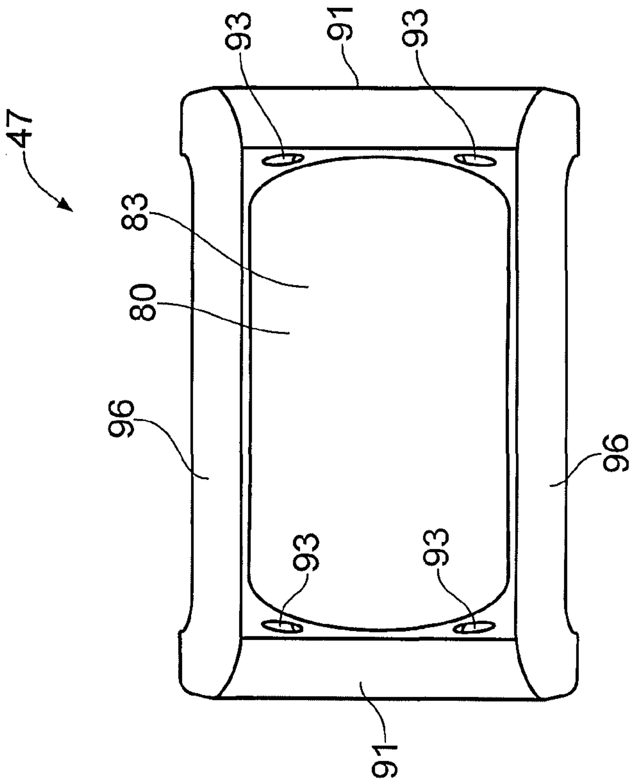
Figure 21:
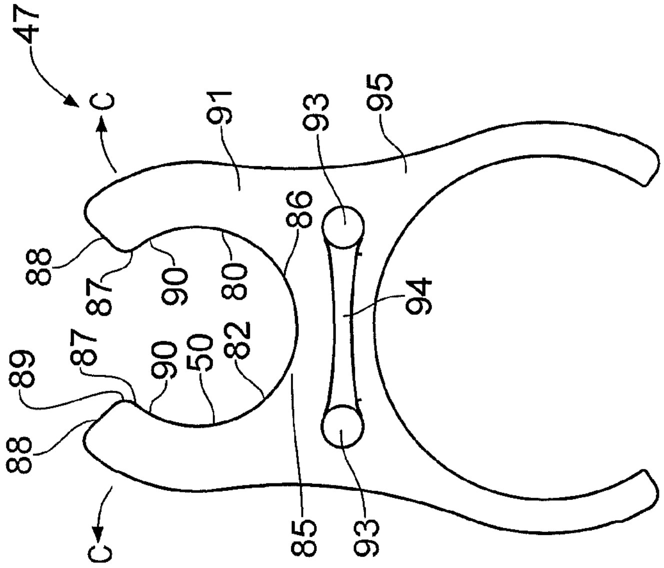
Figure 24:
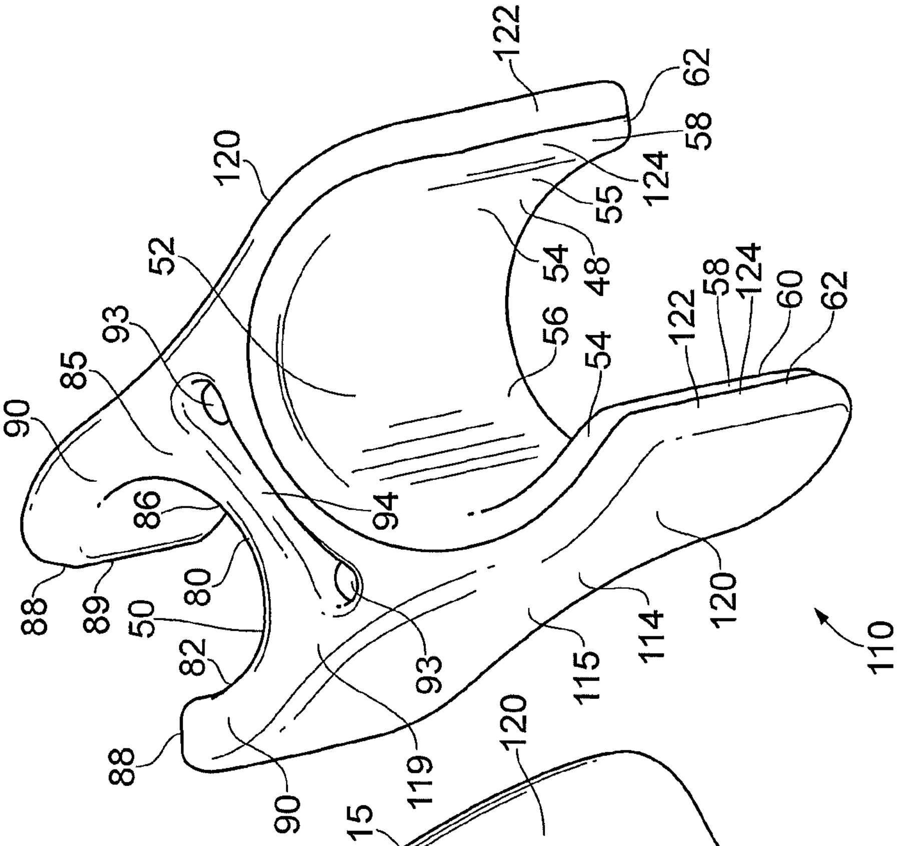
Figure 23:
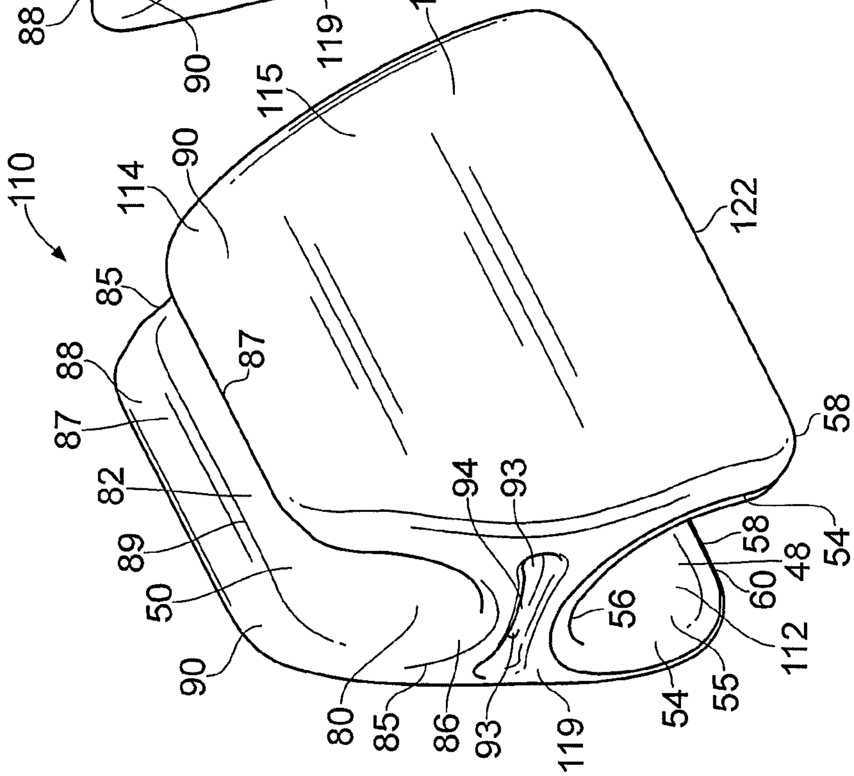
Figure 26:
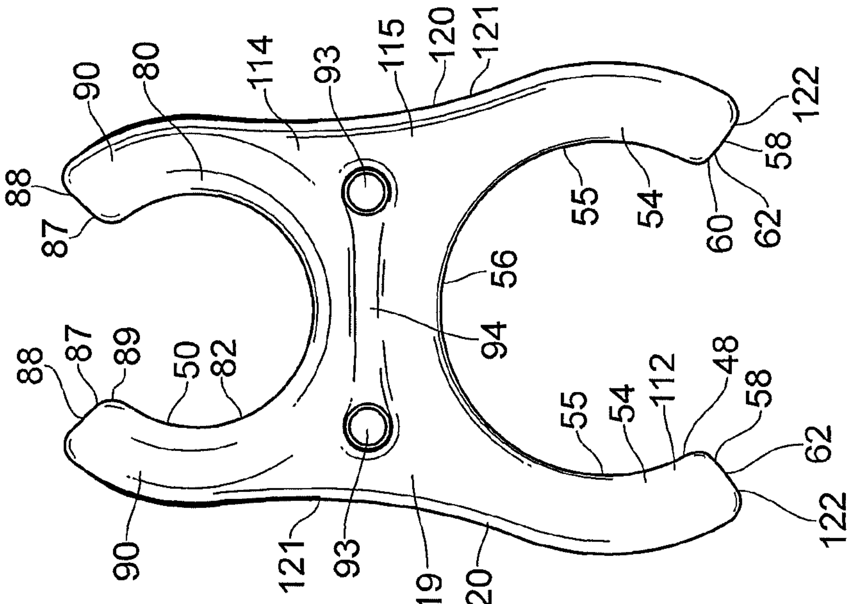
Figure 25:
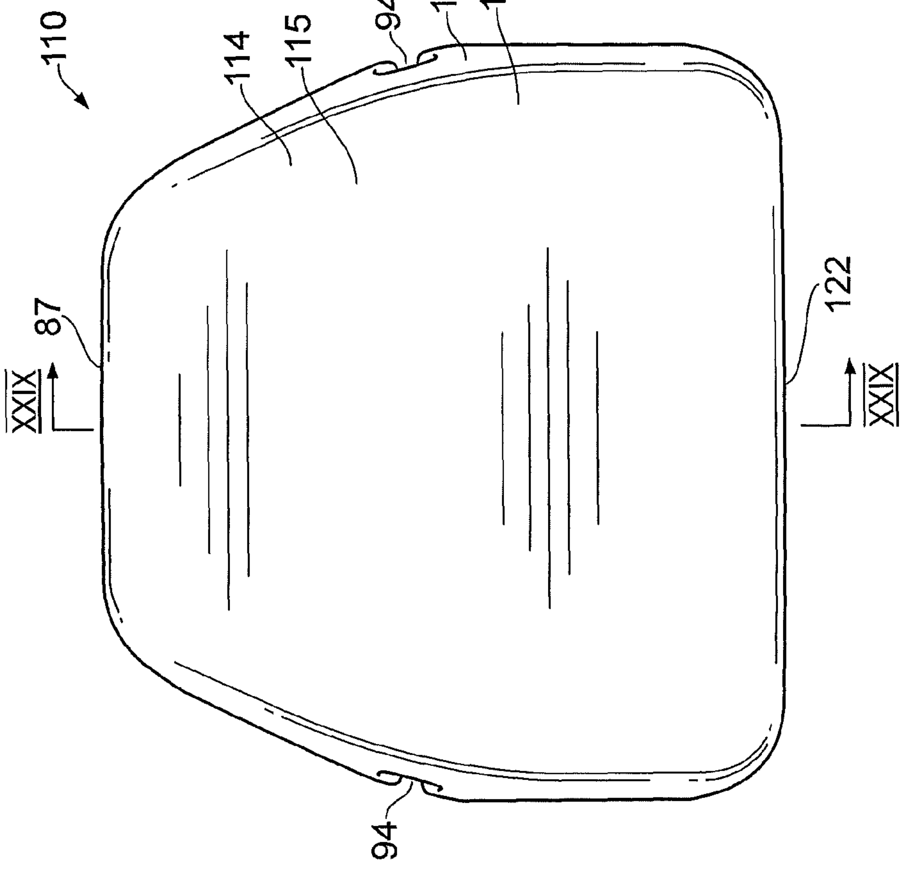
Figure 27:
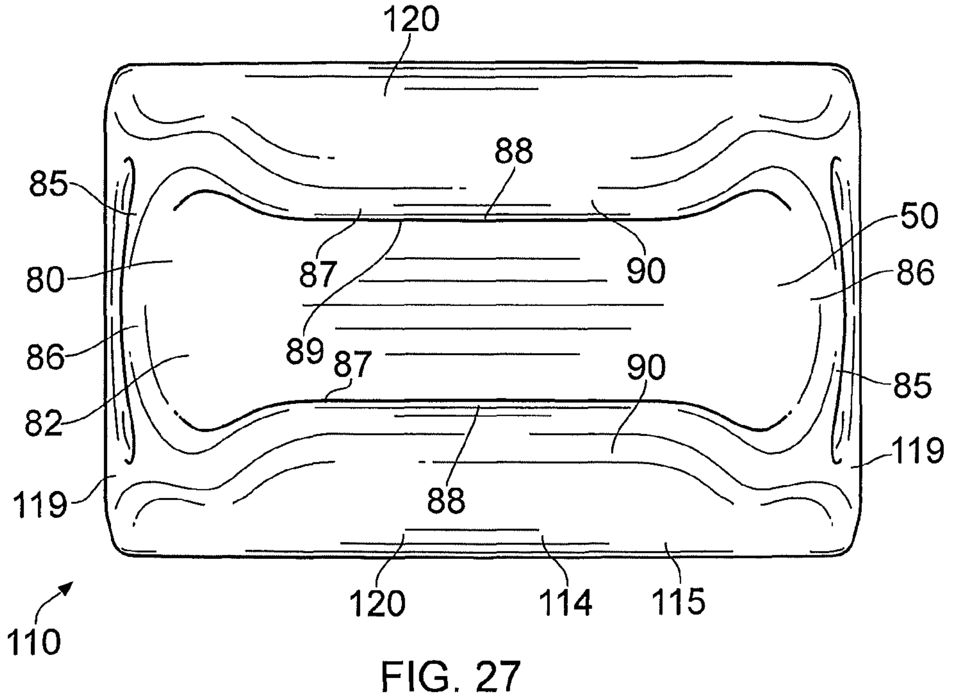
Figure 28:
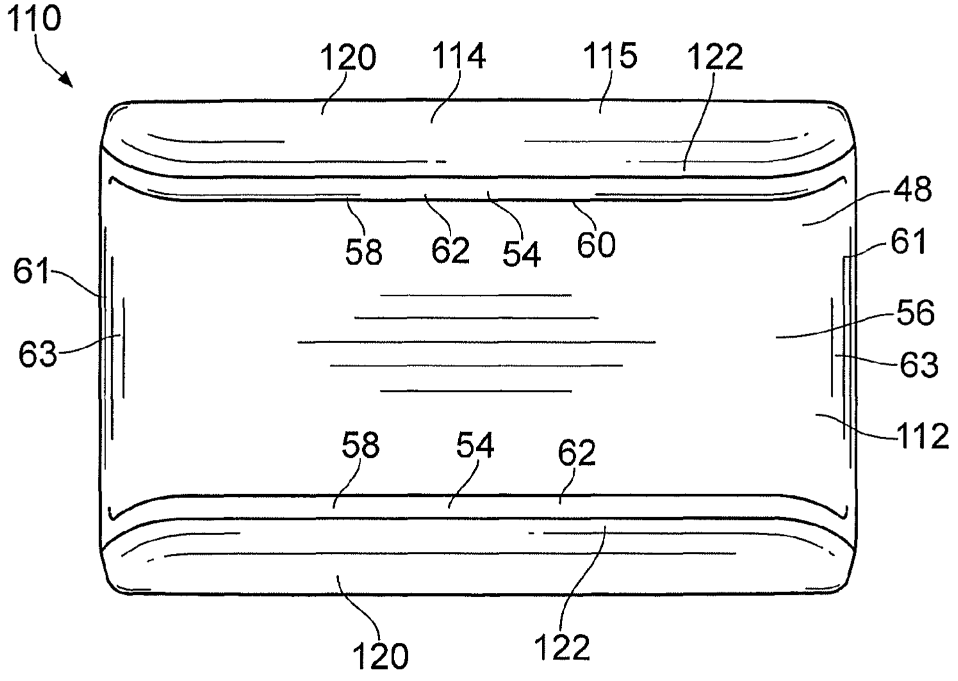
Figures 29, 31, 32:
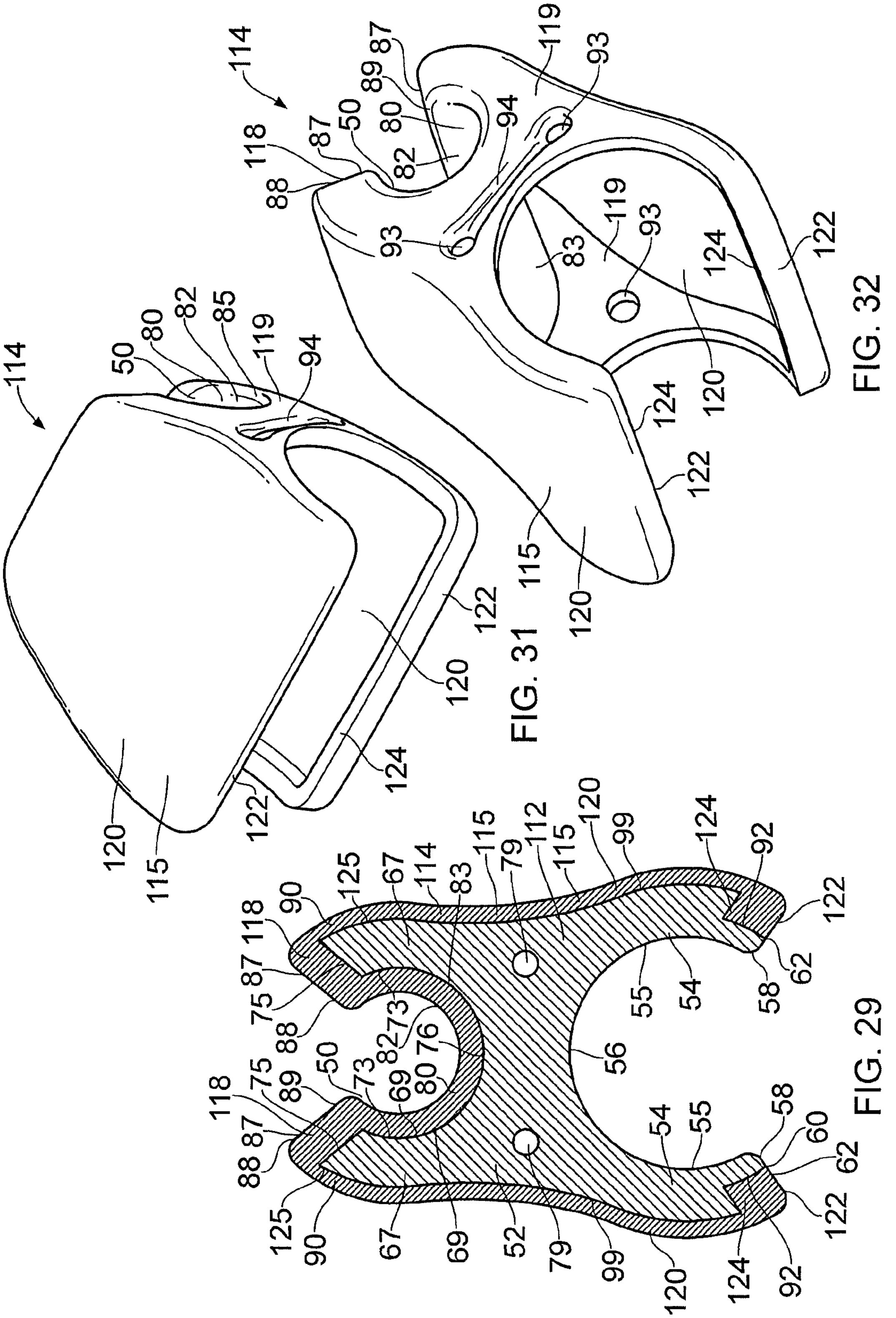
Figure 33:
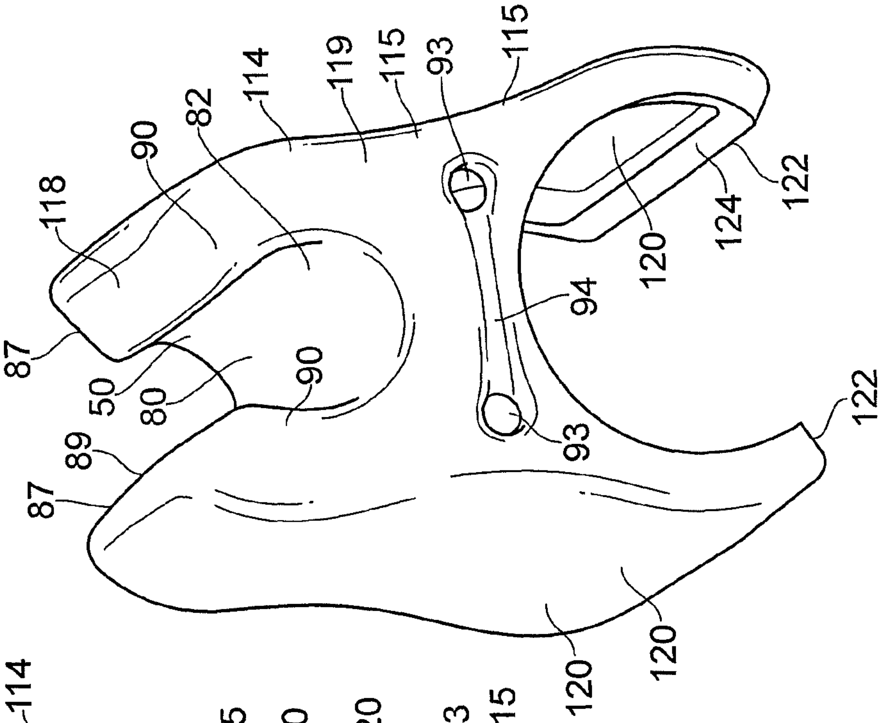
Figure 34:
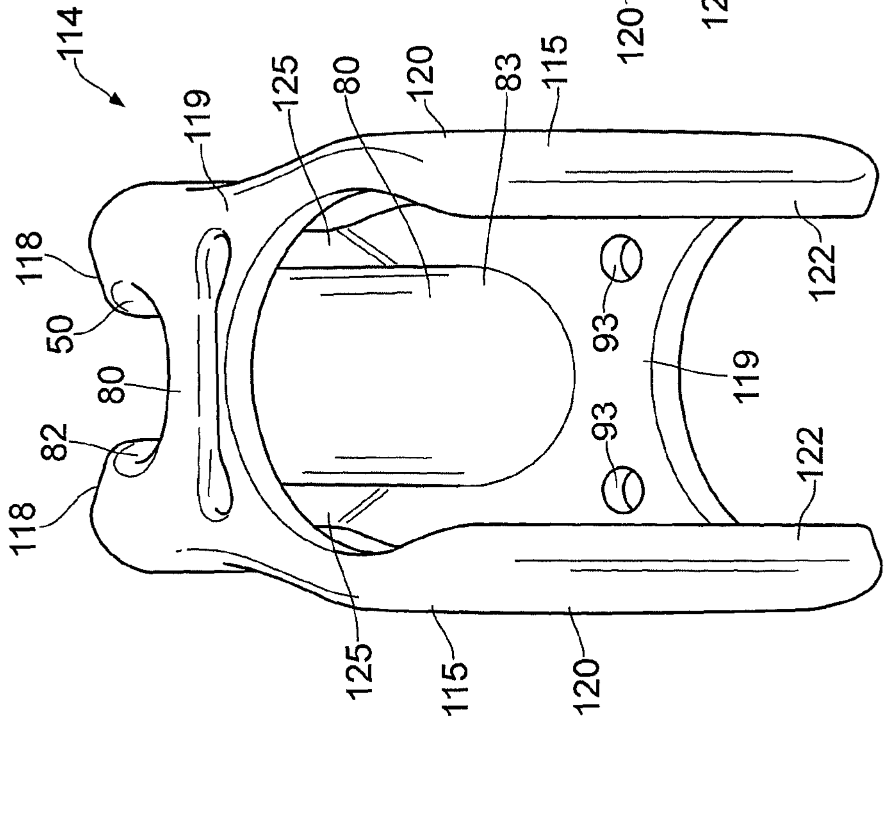
Figure 35:
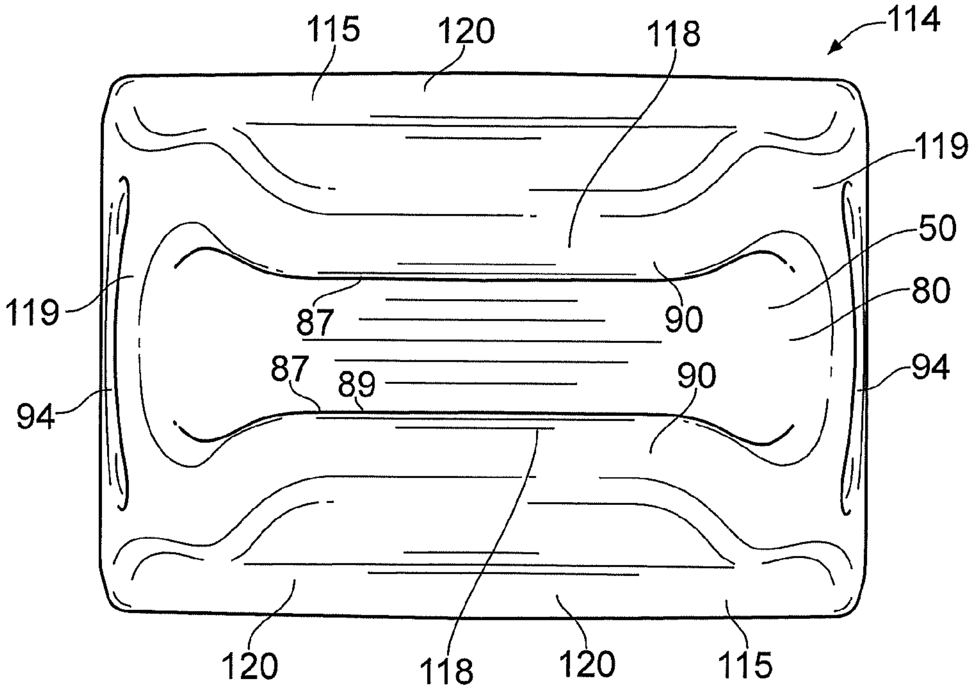
Figure 36:
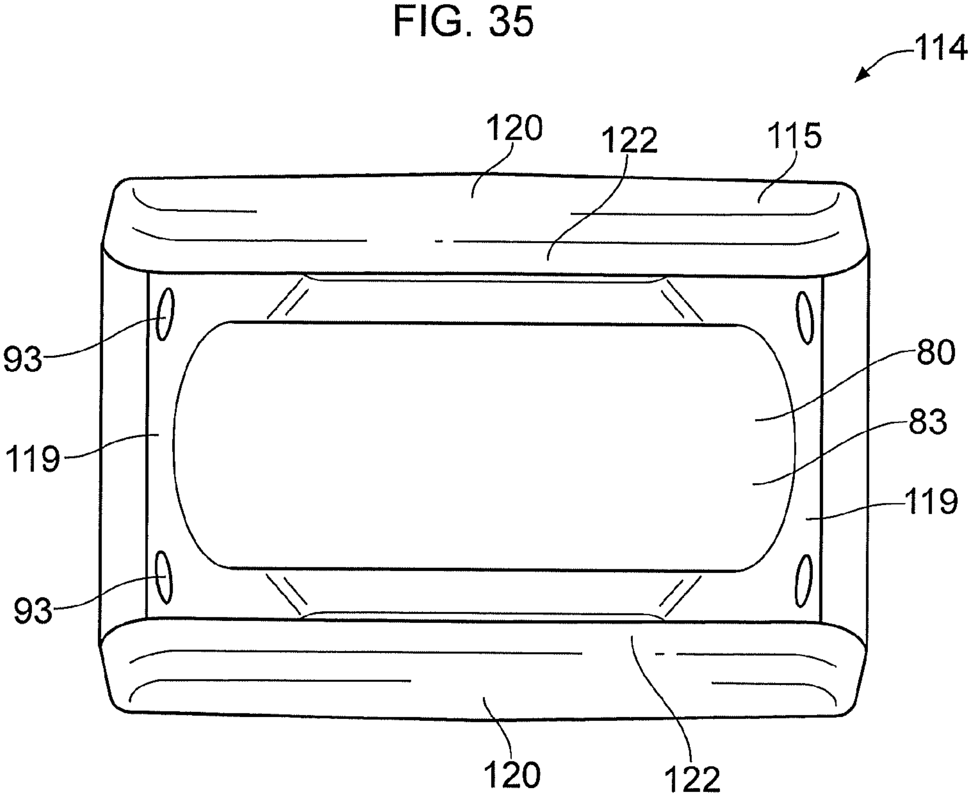
Figure 37:
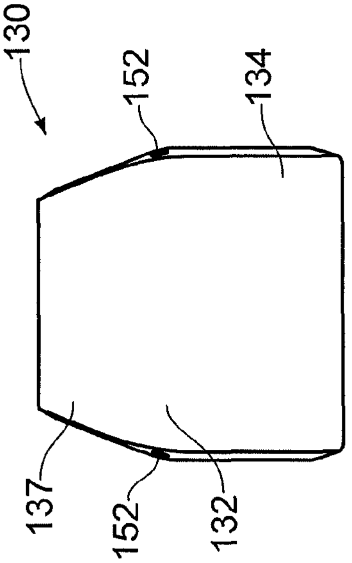
Figure 38:
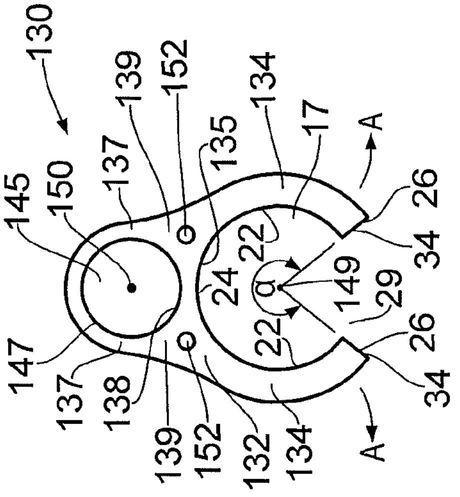
Figure 39:
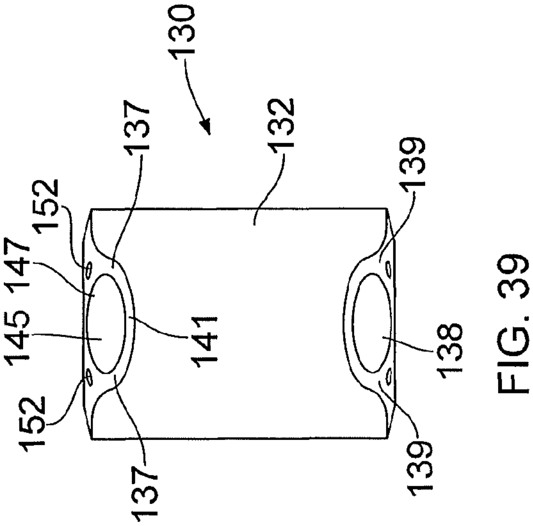
Figure 40:
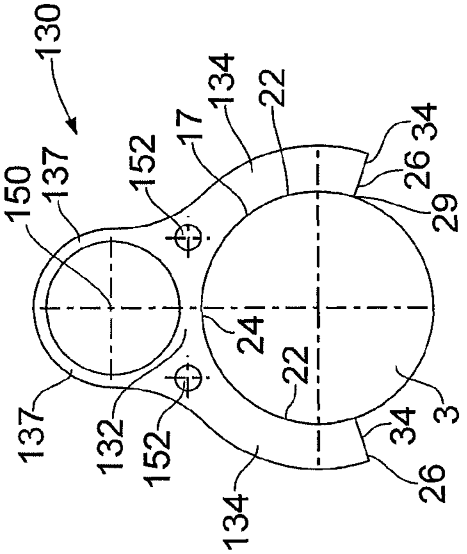

The invention will be more clearly understood from the following description of some preferred embodiments thereof which are given by way of example only with reference to the accompanying drawings, in which:

FIG. 1 is a perspective view of an assembly according to the invention of an endoscope and an elongated tubular member releasably secured to the endoscope by a clip assembly also according to the invention comprising a plurality of clips also according to the invention, FIG. 2 is an exploded perspective view of the assembly of FIG. 1 illustrating the endoscope and the elongated member prior to the elongated member being releasably secured to the endoscope by the clips of FIG. 1, FIG. 3 is an enlarged perspective view of a portion of the assembly of the endoscope and the elongated member of FIG. 1 releasably secured to the endoscope by one of the clips of FIG. 1, FIG. 4 is a side elevational view of the portion of FIG. 3 of the assembly of FIG. 1, FIG. 5 is a perspective view of one of the clips of FIG. 1, FIG. 6 is another perspective view of the clip of FIG. 5, FIG. 7 is a top plan view of the clip of FIG. 5, FIG. 8 is an end elevational view of the clip of FIG. 5, FIG. 9 is a side elevational view of the clip of FIG. 5, FIG. 10 is a side elevational view of the clip of FIG. 5 from the opposite side to that of FIG. 9, FIG. 11 is a perspective view of an assembly according to another embodiment of the invention of an endoscope and an elongated tubular member releasably secured to the endoscope by a clip assembly according to another embodiment of the invention comprising a plurality of clips also according to another embodiment of the invention, FIG. 12 is a perspective view of one of the clips of the clip assembly of FIG. 11 of the invention, FIG. 13 is a transverse cross-sectional end elevational view of the clip of FIG. 12, FIG. 14 is a perspective view of a part of the clip of FIG. 12, FIG. 15 is a side elevational view of the part of FIG. 14 of the clip of FIG. 12, FIG. 16 is an end elevational view of the part of FIG. 14 of the clip of FIG. 12, FIG. 17 is an underneath plan view of the part of FIG. 14 of the clip of FIG. 12, FIG. 18 is a top plan view of the part of FIG. 14 of the clip of FIG. 12, FIG. 19 is a perspective view of another part of the clip of FIG. 12, FIG. 20 is a side elevational view of the part of FIG. 19 of the clip of FIG. 12, FIG. 21 is an end elevational view of the part of FIG. 19 of the clip of FIG. 12, FIG. 22 is an underneath plan view of the part of FIG. 19 of the clip of FIG. 12, FIG. 23 is a perspective view of a clip according to another embodiment of the invention, FIG. 24 is another perspective view of the clip of FIG. 23, FIG. 25 is a side elevational view of the clip of FIG. 23, FIG. 26 is an end elevational view of the clip of FIG. 23, FIG. 27 is a top plan view of the clip of FIG. 23, FIG. 28 is an underneath plan view of the clip of FIG. 23, FIG. 29 is a transverse cross-sectional end elevational view of the clip of FIG. 23 on the line XXIX-XXIX of FIG. 25, FIG. 30 is a side elevational view of a part of the clip of FIG. 23, FIG. 31 is a perspective view of another part of the clip of FIG. 23, FIG. 32 is another perspective view of the part of FIG. 31 of the clip of FIG. 23, FIG. 33 is an end perspective view of the part of FIG. 31 of the clip of FIG. 23, FIG. 34 is an underneath perspective view of the part of FIG. 31 of the clip of FIG. 23, FIG. 35 is a top plan view of the part of FIG. 31 of the clip of FIG. 23, FIG. 36 is an underneath plan view of the part of FIG. 31 of the clip of FIG. 23, FIG. 37 is a side elevational view of a clip according to another embodiment of the invention, FIG. 38 is an end elevational view of the clip of FIG. 37, FIG. 39 is a top plan view of the clip of FIG. 37, and FIG. 40 is an end elevational view of the clip of FIG. 37 illustrated in use.

Referring to the drawings and initially to FIGS. 1 to 10 thereof, there is illustrated an assembly according to the invention indicated generally by the reference numeral 1, in this case an instrument assembly or a surgical instrument assembly 1, comprising a first member, namely, an endoscope 3 and a second member, namely, an elongated member, in this embodiment of the invention an elongated tubular member 5 of an accessory device (not shown), with the tubular member 5 releasably secured to the endoscope 3 by a plurality of spaced apart clips also according to the invention and indicated generally by the reference numeral 7, which are tethered together by a tether 9 to form a clip assembly also according to the invention and indicated generally by the reference numeral 10. The clips 7 and the tethering of the clips 7 to form the clip assembly 10 will be described below. Such endoscopes as the endoscope 3 will be well known to those skilled in the art. The tubular member 5 may be a tube for supplying a liquid or a gas to a cavity in a human or animal body, into which the endoscope 3 is to be inserted, or the tubular member 5 may be a tube for accommodating operating cables to an instrument for operating the instrument in the body cavity. Before describing the clip assembly 10 in further detail, the clips 7 will first be described.

Each clip 7 comprises a body member 12 having a pair of spaced apart first side members 14 extending from a first part 15 of the body member 12 and defining therebetween an elongated first channel 17 for releasably engaging the endoscope 3. A pair of spaced apart second side members 19 extend from a second part 20 of the body member 12, which is opposite to the first part 15 thereof. The second side members 19 extend from the body member 12 in a direction opposite to the direction from which the first side members 14 extend. The second side members 19 define therebetween a passageway, which in this embodiment of the invention comprises a second channel 21 for releasably engaging the tubular member 5. The first and second channels 17 and 21 extend parallel to each other so that the tubular member 5 and the endoscope 3 extend parallel to each other when releasably secured together by the clips 7.

The first and second side members 14 and 19 define inner concave surfaces 22 and 23, respectively, of the first and second channels 17 and 21. The first and second parts 15 and 20 of the body member 12 each also define respective concave surfaces 24, which together with the inner concave surfaces 22 and 23 of the corresponding first and second side members 14 and 19 define the first and second channels 17 and 21, respectively. In this embodiment of the invention the concave surfaces 24 defined by the first and second parts 15 and 20 of the body member 12 and the inner concave surfaces 22 and 23 of the first and second side members 14 and 19, respectively, define the first and second channels 17 and 21 to be of partly circular transverse cross-section. The first and second channels 17 and 21 define respective longitudinally extending first and second central axes 16 and 18, which extend parallel to each other.

The first side members 14 terminate in longitudinally extending spaced apart parallel first distal side edges 25, which define a first open mouth 27 for accommodating the endoscope 3 into the first channel 17. The first distal side edges 25 define respective first lead-ins 34 converging inwardly towards the first channel 17 for accommodating the endoscope 3 into and through the first open mouth 27. The first channel 17 extends around the first central axis 16 between the first distal side edges 25 an angular distance $\alpha$ of approximately 250°.

The second side members 19 terminate in longitudinally extending spaced apart parallel second distal side edges 26, which define a second open mouth 29 for accommodating the tubular member 5 into the second channel 21. The second distal side edges 26 define respective second lead-ins 35 converging inwardly towards the second channel 21 for accommodating the tubular member 5 into and through the second open mouth 29. The second channel 21 extends around the second central axis 18 between the second distal side edges 26 through an angle $\theta$ greater than 180°, which in this embodiment of the invention is an angle of approximately 273°.

The resilience of the first and second side members 14 and 19 is such that the first and second side members 14 and 19 are urgeable outwardly in the direction of the arrows A and B, respectively, for accommodating the endoscope 3 and the tubular member 5 into the respective first and second channels 17 and 21 through the first and second open mouth 27 and 29 thereof. The diameter of the first channel 17 is less than the diameter of the endoscope 3, and the diameter of the second channel 21 is less than the diameter of the tubular member 5. Thus when the endoscope 3 and the tubular member 5 are located in the first and second channels 17 and 21, respectively, the endoscope 3 and the tubular member 5 are releasably engaged and gripped tightly in the first and second channels 17 and 21 by the respective first and second side members 14 and 19. The resilience of the material of the first and second side members 14 and 19 is such that the first and second side members 14 and 19 are biased inwardly into engagement with the endoscope 3 and the tubular member 5, respectively, by resilient forces acting in the first and second side members 14 and 19 biasing the first and second side members 14 and 19 inwardly to their respective natural relaxed states from their deformed states in order to accommodate the endoscope 3 and the tubular member 5 in the first and second channels 17 and 21.

In this embodiment of the invention the first and second side members 14 and 19 are integrally formed in one piece with the body member 12 by injection moulding from a resilient plastics material.

A pair of tether accommodating apertures for accommodating the tether 9 therethrough in this embodiment of the invention comprise respective spaced apart tether accommodating bores 28. The tether accommodating bores 28 extend through the body member 12 parallel to each other and parallel to the first and second central axes 16 and 18 of the first and second channels 17 and 21, respectively, for accommodating the tether 9 therethrough.

Referring now to FIGS. 1 and 2 the clip assembly 10 of the clips 7 tethered by the tether 9 will now be described. The tether 9 is formed into an endless loop 30 having a first leg 31 and a second leg 32. The first leg 31 of the looped tether 30 freely engages one of the tether accommodating bores 28 in each clip 7 with the clips 7 in series. The second leg 32 of the looped tether 30 freely engages the other one of the tether accommodating bores 28 of the respective clips 7 with the clips 7 similarly in series. With the first and second legs 31 and 32 of the looped tether 30 extending through the tether accommodating bores 28 of the clips 7 free ends of the tether 9, for example, free ends at the end 33 of the tether 9 are secured together by tying or by other suitable securing means to form the endless looped tether 30. End grooves 36 extend into the body member 12 of each clip 7 adjacent the opposite ends thereof between the tether accommodating bores 28 for accommodating the opposite ends of the looped tether 30 recessed into the end grooves 36 of the two clips 7 at the extreme ends 37 of the looped tether 30. With the clip assembly 10 of the clips 7 secured together on the looped tether 30, the clip assembly 10 of the clips 7 is ready for use.

Typically, the clips 7 are releasably secured to the endoscope 3 at spaced apart locations along the endoscope 3 by engaging the endoscope 3 in the first channels 17 of the clips 7. Since the first side members 14 forming the first channel 17 of each clip 7 are resilient, the side members 12 diverge outwardly from each other as each clip 7 is being engaged on the endoscope 3. Once the endoscope 3 is fully engaged in the first channel 17, the first side members 14 are resiliently biased towards each other towards their relaxed states, and therefore, into tight secure engagement with the endoscope 3, and with the first side members 14 embracing approximately 250° of the endoscope 3.

Once the clips 7 have been releasably secured to the endoscope 3, the tubular member 5 is then releasably secured to the endoscope 3 by the clips 7. The tubular member 5 is engaged in the second channels 21 of the clips 7, in similar manner as described with reference to the engagement of the endoscope 3 in the first channels 17 of the clips 7, with the second side members 19 embracing approximately 273° of the tubular member 5. However, the second channel 21 may be adapted to either tightly engage the tubular member 5 or to slideably engage the tubular member 5, whereby the tubular member 5 would be longitudinally slideable in the second channel 21.

With the tubular member 5 releasably secured to the endoscope 3 by the clips 7 to form the assembly 1 of the endoscope 3 and the tubular member 5, the assembly 1 of the endoscope 3 and the tubular member 5 is ready for use.

The assembly 1 of the endoscope 3 and the tubular member 5 releasably secured together by the clip assembly 10 is inserted through the appropriate orifice, orally, nasally or rectally into a body cavity of a subject in which an investigative or surgical procedure is to be carried out. On completion of the investigative or surgical procedure, the assembly 10 of the endoscope 3 and the tubular member 5 is then removed from the body cavity.

Since the clips 7 are tethered in series by the looped tether 30, even if one or more of the clips 7 become detached from both the endoscope 3 and the tubular member 5, the detached clip or clips 7 will be retained captive on the looped tether 30, and will therefore be automatically removed from the subject as the endoscope 3 and the tubular member 5 are being withdrawn therefrom.

Accordingly, the advantage of the clip 7 and the clip assembly 10 of the tethered clips 7 according to the invention is that there is no danger of a clip 7 which may become detached from the endoscope 3 and the tubular member 5 remaining in the body cavity or other part of the body of a subject on withdrawal of the endoscope 3 and the tubular member 5, since all the clips 7 are retained captive together by the loop tether 30.

Referring now to FIGS. 11 to 22 there is illustrated a clip according to another embodiment of the invention indicated generally by the reference numeral 40. In FIG. 11 a plurality of the clips 40 are illustrated tethered together by a tether 41, similar to the tether 7 of the clip assembly 10 described with reference to FIGS. 1 to 10, to form a clip assembly also according to the invention and indicated generally by the reference numeral 42 for securing a first member, for example, an endoscope 3, and a second member, for example, a tubular member 5 together to form an assembly also according to the invention and indicated generally by the reference numeral 43, namely, an instrument assembly or a surgical instrument assembly 43 comprising the endoscope 3 and the tubular member 5.

In this embodiment of the invention each clip 40 comprises a two-part clip which comprises a carrier element 45 and an adapter element 47, which may be either releasably or non-releasably secured to the carrier element 45, or may be insert moulded onto the carrier element 45. When the adapter element 47 is secured to the carrier element 45 to form the clip 40, the clip 40 defines an elongated first channel 48 for releasably engaging the first of the two members to be secured together, namely, the endoscope 3, and an elongated passageway, which in this embodiment of the invention comprises an elongated second channel 50 for releasably engaging the second member, namely, the tubular member 5 of the first and second members to be secured together. The first channel 48 is adapted to tightly but releasably grip the endoscope 3. The second channel 50 may be adapted to either tightly or slideably engage the tubular member 5. The first channel 48 defines a longitudinally extending first central axis 49. The second channel 50 defines a longitudinally extending second central axis 51 which extends parallel to the first central axis 49 defined by the first channel 48.

The carrier element 45 comprises a plastics material, and the adapter element 47 also comprises a plastics material. The plastics materials of the carrier element 45 and the adapter element 47 are resilient materials, but have different resilient characteristics. The resilience of the plastics material of the carrier element 45 is of a greater strength than the resilience of the plastics material of the adapter element 47, in that it takes a greater force or pressure to deform the plastics material of the carrier element 45 than that which is required to deform the plastics material of the adapter element 47. In other words, the plastics material of the adapter element 47 is more elastic and yielding than the plastics material of the carrier element 45. Additionally, the plastics material of the adapter element 47 is a softer material than the plastics material of the carrier element 45.

Turning now to the carrier element 45, and referring to FIGS. 14 to 18, the carrier element 45 comprises a body member 52. A pair of spaced apart arcuate first side members 54 extend from the body member 52 with the body member 52 defining with the first side members 54 the first channel 48 of partly circular transverse cross-section. The first side members 54 each define an inner concave surface 55, which faces towards the concave surface 55 of the other first side member 54 for defining a part of the first channel 48. The part of the body member 52 which defines a part of the first channel 48 also defines a concave surface 56 which with the concave surfaces 55 of the first side members 54 define the first channel 48.

The first side members 54 terminate in respective longitudinally extending first distal side edges 58. The first distal side edges 58 of the first side members 54 define an elongated longitudinally extending first open mouth 60 for accommodating the endoscope into the first channel 48. The first distal side edges 58 of the first side members 54 are angled to define first lead-ins 62, which converge inwardly towards the first channel 48, to accommodate the endoscope 3 into and through the first open mouth 60 into the first channel 48. The first channel 48 extends around the first central axis 49 between the first distal side edges 58 an angular distance α of approximately 250°. The first side members 54 are inherently resilient, and are resiliently urgeable apart from each other in the directions of the arrows A to accommodate the endoscope 3 into the first channel 48. In this embodiment of the invention the diameter of the first channel 48 is less than the diameter of the endoscope 3, so that the endoscope 3 is tightly gripped and retained in the first channel 48 by the resilient inward biasing action of the first side members 54 towards each other on the endoscope 3 due to the first side members 54 being resiliently biased towards their relaxed state from their deformed state.

The first side members 54 and the body member 52 terminate at their respective opposite ends 61 to define the respective opposite ends 63 of the first channel 48. Portions 64 of the first side members 54 are relieved along the first distal side edges 58 thereof, and portions 65 of the ends 61 of the first side members 54 and the body member 52 are relieved for purposes to be described below.

A pair of spaced apart arcuate engagement side members 67 extend from the body member 52 in an opposite direction to the direction from which the first side members 54 extend therefrom. The engagement side members 67 define with the body member a first passageway, in this embodiment of the invention, an engagement channel 69 of partly circular transverse cross-section. The engagement channel 69 as will be described below is configured for engaging the adapter element 47, or to form the second channel 50 to engage the second member, namely, the tubular member 5. The engagement channel 69 defines a first passageway central axis, in this case a central engagement channel axis 68, which when the adapter element 47 is engaged in the engagement channel 69 coincides with the second central axis 51.

The engagement side members 67 define opposite concave arcuate surfaces 73, which face each other and define a part of the engagement channel 69. A portion of the body member 52 also defines a concave surface 76, which with the concave surfaces 73 defined by the engagement side members 67, define the engagement channel 69 of partly circular transverse cross-section. The engagement side members 67 terminate in respective longitudinally extending spaced apart distal side edges 75, which define a longitudinally extending open mouth 77 for accommodating the adapter element 47 therethrough into the engagement channel 69. The engagement channel 69 extends around the central engagement channel axis 68 between the distal side edges 75 defined by the engagement side members 67 an angular distance D of approximately 273°. The engagement side members 67 are inherently resilient, and are resiliently urgeable outwardly in the directions of the arrow B for accommodating the adapter element 47 or the tubular member 5, as the case may be, into the engagement channel 69. The diameter of the engagement channel 69 is such, that as will be described below, when the adapter element 47 is located in the engagement channel 69 the adapter element 47 is tightly engaged and gripped therein by the resilient action of the engagement side members 67 acting on the adapter element 47.

A pair of parallel spaced apart tether accommodating apertures, in this embodiment of the invention, tether accommodating bores 79 extend longitudinally through the body member 52 parallel to both the first central axis 49 and the central engagement channel axis 68 for accommodating the tether 41 therethrough for joining a plurality of the clips 40 to form the clip assembly 42 in a similar manner as the clip assembly 10 as described with reference to FIGS. 1 to 10.

In this embodiment of the invention the carrier element 45 is integrally formed in one piece of plastics material by injection moulding. As discussed above, the plastics material of the carrier element 45 is of resilience such that the first side members 54 are sufficiently resilient to resiliently grip and retain the endoscope 3 in the first channel 48, and such that the engagement side members 67 are sufficiently resilient to resiliently grip and retain the adapter element 47, and depending on the diameter of the tubular member 5, the engagement side members 67 either slideably engage or tightly engage the tubular member 5 in the engagement channel 69.

Turning now to the adapter element 47, and referring to FIGS. 19 to 22, the adapter element 47 comprises an engagement portion having a second passageway extending therethrough for accommodating the tubular member 5 or other such second member therethrough. In this embodiment of the invention the engagement portion of the adapter element 47 comprises an arcuate element 80 having an inner arcuate surface 82 and an outer arcuate surface 83. The inner arcuate surface 82 is of partly circular transverse cross-section and defines the second passageway as the second channel 50, and in turn defines the second central axis 51. The outer arcuate surface 83 of the arcuate element 80 defines the engagement channel 69, and is engageable in the engagement channel 69 of the carrier element 45. The transverse cross-sectional diameter of the outer arcuate surface 83 of the arcuate element 80 is greater than transverse cross-sectional diameter of the engagement channel 69, so that the arcuate element 80 is tightly engaged in the engagement channel 69 by the resilient inward biasing action of the engagement side members 67 towards each other on the arcuate element 80 resulting from the outward deformation of the engagement side members 67 to accommodate the arcuate element in the engagement channel 69.

The arcuate element 80 extends between respective opposite ends 85 which define the opposite ends 86 of the second channel 50.

The arcuate element 80 extends around the second central axis 51 and terminates in respective longitudinally extending spaced apart second distal side edges 87 which define an elongated longitudinally extending open mouth 89 for accommodating the tubular member 5 into the second channel 50. The second distal side edges 87 define second lead-ins 88 which converge inwardly towards the second channel 50 for accommodating entry of the tubular member 5 into and through the second open mouth 89 into the second channel 50. The arcuate element 80 extends around the second central axis 51 an angular distance θ of between 273° and 292°, as will be described below. The resilience of the plastics material of the arcuate element 80 and the resilience of the engagement side members 67 of the carrier element 45 are such that side portions 90 of the arcuate element 80, and in turn the second distal side edges 87 along with the engagement side members 67 of the carrier element 45 are urgeable away from each other in the direction of the arrow C for accommodating the tubular member 5 through the open mouth 89 into the second channel 50. Additionally, the resilience of the side portions 90 of the arcuate element 80 and the resilience of the engagement side members 67 of the carrier element 45 is such as to resiliently grip and retain the tubular member 5 in the second channel 50 if the diameter of the tubular member 5 is greater than the diameter of the inner arcuate surface 82 of the arcuate element 80 in its relaxed state, for the same reason that the first side members 54 resiliently engage and grip the endoscope 3 as discussed above. Otherwise, the tubular member 5 is slideable in the second channel 50.

A covering element 95 of the adapter element 47 for covering at least a portion of the external surface 99 of the carrier element 45, in this embodiment of the invention covers the relieved portions 65 at the respective opposite ends of the carrier element 45, and the relieved portions 64 extending along and adjacent the first distal side edges 58 of the first side members 54. The covering element 95 comprises respective end panels 91 extending sidewardly outwardly and downwardly from the arcuate element 80 at the respective opposite ends 85 thereof for covering the relieved portions 65 of the ends 61 of the body member 52. Lower portions 96 of the covering element 95 extend between the end panels 91 for covering the relieved portions 64 of the first side members 54 adjacent the first distal side edges 58 thereof. The lower portions 96 form a securing means for securing the adapter element 47 to the carrier element 45, and act as securing members, and engage the relieved portions 64, which form receiving recesses 92. In this embodiment of the invention the lower portions 96 engage the receiving recesses 92 with a snap-fit action when the arcuate element 80 is engaged in the engagement channel 69.

A pair of engagement recesses 98 are formed into the outer surface 83 of the arcuate element 80 and extend along the outer surface 83 thereof adjacent the second distal side edges 87 of the arcuate element 80 for engaging the respective distal side edges 75 of the engagement side members 67.

The cooperating action between the arcuate element 80 in the engagement channel 69, the distal side edges 75 of the engagement side members 67 in the engagement recesses 98 of the arcuate element 80, and the lower portions 96 in the receiving recesses 92 of the carrier element 45 and the end panels 91, retain the adapter element 47 secured to the carrier element 45.

Respective spaced apart pairs of parallel tether accommodating apertures 93 extend through the respective end panels 91 of the adapter element 47 for accommodating the tether 41 therethrough. The tether accommodating apertures 93 of the adapter element 47 are aligned with the tether accommodating bores 79 of the carrier element 45 when the adapter element 47 is secured to the carrier element 45. Transversely extending end grooves 94 extend into the respective end panel 91 between the corresponding pair of tether accommodating apertures 93 for accommodating end parts of the looped tether 41 therein in the clips 40 at the extreme ends of the looped tether 41 between the tether accommodating apertures 93.

The adapter element 47 with the arcuate element 80, the end panels 91 and the lower portions 96, as discussed above, are of resilient plastics material, and are integrally formed in one piece by injection moulding.

To assemble the adapter element 47 to the carrier element 45, the adapter element 47 is fitted onto the carrier element 45 by urging the arcuate element 80 into engagement with the engagement channel 69 of the carrier element 45, with the distal side edges 75 of the engagement side members 67 engaging the engagement recesses 98 in the arcuate element 80, and with the end panels 91 abutting the ends 61 of the body member 52. Once the arcuate element 80 is engaged in the engagement channel 69 and the distal side edges 75 of the engagement side members 67 are engaged in the engagement recesses 98, the lower portions 96 of the covering element 95 are engaged in the receiving recess 92 extending along the first side members 54 adjacent the first distal side edges 58 thereof with a snap-fit action, for in turn securing the adapter element 47 to the carrier element 45. Once the adapter element 47 has been secured to the carrier element 45, the clip 40 is ready for use.

If the clip is to be used with a plurality of other clips 40 tethered together to form the clip assembly 42, the clips 40 are assembled with the looped tether 41 extending through the tether accommodating bores 79 of the clips 40.

To secure a second elongated member to a first elongated member by the clip assembly 42, the first member, for example, the endoscope 3, is secured to the clips 40 of the clip assembly 42 by engaging the endoscope 3 in the first channels 48 in each of the clips 40 sequentially. The second member, for example, the tubular member 5, is then engaged sequentially in the second channels 50 of the clips 40 of the clip assembly 42.

The assembly 43 comprising the tubular member 5 secured to the endoscope 3 by the clip assembly 42 is ready for use. The endoscope 3 with the tubular member 5 secured thereto by the clip assembly 42 may then be entered into a subject orally, nasally or rectally to a cavity in the subject in which an investigative of surgical procedure is to be carried out.

It is envisaged that a plurality of the clips 40 will be provided with the second channels of respective differing transverse cross-sectional diameter for securing tubular or other second members of different diameter to the first member. It is envisaged that clips 40 with second channels 50 of, for example, three different internal diameters may be provided. The clip 40 with the second channel 50 of the smallest internal diameter, may be provided with the second channel 50 of internal diameter of approximately 3 mm. The clip 40 with the second channel 50 of the largest internal diameter may be provided with the second channel 50 of internal diameter of approximately 6 mm. The clip 40 with the second channel 50 of medium internal diameter may be provided with a second channel 50 of internal diameter of approximately 4.5 mm.

In the clip 40 of the second channel 50 of the smallest internal diameter, the second channel 50 may extend around the second central axis 51 between the first distal side edges 87 an angular distance of approximately 292°. The corresponding angular distance for the second channel 50 of the largest diameter may be 273°, while the corresponding angular distance for the second channel 50 of the medium diameter may be 282°.

It is envisaged that the carrier elements 45 of the clips 40 will be of similar external dimensions, irrespective of the internal diameter of the second channel 50.

It is envisaged that one of the clips 40, of which the second channel 50 is to be of the largest internal diameter, that clip 40 may be provided with the second channel being formed by the engagement channel 69 of the carrier element 45. In which case the engagement portion of the adapter element 47 would comprise the arcuated portions of the end panels 91, which form the respective ends 85 of the second channel and the lead-ins 88.

In this embodiment of the invention when it is desired to utilise the clip 40 for securing an elongated tubular member 5 of circular transverse cross-section to an endoscope 3 of, for example, outer diameter of 9 mm, it is envisaged that the internal diameter of the first channel 48 in its relaxed or non-deformed state, may be of internal diameter of approximately 8.5 mm.

In this embodiment of the invention the clip 40 has been described as being formed as two separate parts, where the carrier element 45 and the adapter element 47 are provided as two separate parts, and subsequently assembled. However, the clip 40 may be provided in one-piece form, in which case, it is envisaged that the clip 40 would be formed by insert moulding, whereby the adapter element 47 would be insert moulded onto the carrier element 45. In other words, the carrier element 45 would be injection moulded or otherwise formed, and when formed would then be placed in a suitable insert mould, and the adapter element 47 would be moulded onto the carrier element 45 in a suitable insert moulding process. In cases where the adapter element 47 is insert moulded onto the carrier element 45, the melt temperature of the material of the adapter element 47 would be lower than the melt temperature of the material of the carrier element 45 in order to avoid any melting or deterioration of the carrier element 45 during the insert moulding of the adapter element 47 onto the carrier element 45.

The clip 40 according to this embodiment of the invention provides a particularly important advantage, in that since the adapter element 47 is of a resilient material which is more easily deformable, and can be deformed with less force than the resilient material of the carrier element 45, and in particular, since the material of the adapter element 47 is more yielding and elastic and softer than the material of the carrier element 45, the risk of the clips 40 resulting in any injury or damage to the inner surface or the inner lining of a lumen, vessel or cavity, through which the endoscope 3 with the tubular member 5 clipped thereto by the clip assembly 42 is being urged, such as grazing, bruising or rupturing of the inner surface or the inner lining of the vessel, lumen or cavity, is minimised, since the respective opposite ends 61 and the edges of the carrier element 45 are covered by the covering element 95 of the adapter element 47, which is of a more elastic and softer resilient material than that of the carrier element 45.

It will of course be appreciated that while the clips 40 have been described as forming a clip assembly 42, the clip 40 may be provided with or without the tether accommodating bores and apertures, and in general, would only be provided with the tether accommodating bores and apertures if two or more of the clips were to be secured together by a tether or a looped tether.

It will of course be appreciated that the transverse cross-sections of the first and the second channels may be of any suitable transverse cross-sectional shape or size, and in general, it is envisaged that the transverse cross-section of the first and second channels will be provided to be suitable for engaging instruments or tubular members of specific transverse cross-sectional dimensions, and also specific transverse cross-sectional shapes.

It is also envisaged that while the second channel has been described as being configured to grip a tubular member or other member or instrument, the tubular member or other member or instrument could be slideable or otherwise moveable in the second channel. It is also envisaged that the first channel may be configured so that the endoscope or other member could be slideable or otherwise moveable in the first channel.

It is also envisaged that an arcuate element similar to the arcuate element 80 may also be located in the first channel or be provided to be inserted into the first channel, for example, to reduce the transverse cross-sectional diameter of the first channel, in which case the arcuate element for the first channel could be formed integrally with the adapter element, or the arcuate element for the first channel could be provided separately from the adapter element.

It is also envisaged that a plurality of arcuate elements could be provided for insertion in the first channel, the arcuate elements defining first channels of respective different transverse cross-sectional diameters to accommodate endoscopes or other members or instruments of different transverse cross-sectional diameters.

Alternatively, it is envisaged that the adapter element may be configured with the arcuate element configured for locating in the first channel instead of in the engagement channel. In other words, only the first channel would have an arcuate element located therein, there would be no arcuate element located in the engagement channel, and the engagement channel would form the second channel. However, as discussed above either the adapter element may be provided with two arcuate elements, one for the engagement channel and one for the first channel, or the adapter element may be provided with one arcuate element only for either the first channel or the engagement channel, and a separate arcuate element separate from the adapter element may be provided for the other one of the first channel and engagement channel.

Referring now to FIGS. 23 to 36 there is illustrated a clip according to another embodiment of the invention indicated generally by the reference numeral 110 for releasably securing first and second members together. The clip 110 is substantially similar to the clip 40, and similar components are identified by the same reference numerals. The clip 110 comprises a carrier element 112 and an adapter element 114. The carrier element 112 of the clip 110 is substantially similar to the carrier element 45 of the clip 40 and similar components are identified by the same reference numerals. The only difference between the carrier element 45 of the clip 40 and the carrier element 112 is that the respective opposite ends 63 of the first channel 48 do not project beyond the end portions 65 of the carrier element 45, see FIG. 30. The adapter element 114 of the clip 110 is substantially similar to the adapter element 47 of the clip 40, and similar components are also identified by the same reference numerals. The main difference between the adapter element 114 and the adapter element 47 of the clip 40 lies in the covering element. In this embodiment of the invention the adapter element 114 comprises a covering element 115 which substantially covers the entire external surface 99 of the carrier element 112.

In this embodiment of the invention the covering element 115 of the adapter element 114 comprises end panels 119 extending sidewardly outwardly and downwardly from the respective opposite ends 85 of the arcuate element 80, which are similar to the end panels 91 of the adapter element 41 of the clip 40. However, in this embodiment of the invention side panels 120 cover opposite side surfaces 121 of the carrier element 112. The side panels 120 extend between the end panels 119 and extend downwardly from lead-in forming members 118, which extend along the side edges 87 of the arcuate element 80 and outwardly therefrom. The side panels 120 extend downwardly from the lead-in forming members 118 and terminate in respective opposite longitudinally extending side edges 122 in elongated longitudinally extending securing members 124 for engaging the corresponding receiving recesses 92, formed in the first side members 54 and extending longitudinally along and adjacent the respective first distal side edges 58 thereof, with a snap-fit action to retain the adapter element 114 secured to the carrier element 112.

The end panels 119 and the side panels 120 together with the arcuate element 80 and the lead-in forming members 118 of the adapter element 114 define respective engagement recesses 125 for engaging the corresponding engagement side members 67 of the carrier element 112 therein. The securing members 124 extending longitudinally along the side edges 122 of the side panels 120 engage the receiving recesses 92 and cooperate with the end panels 119 and the arcuate element 80 for retaining the adapter element 114 on and secured to the carrier element 112 in a similar manner as the lower portions 96 and the end panels 91 cooperate with the arcuate element 80 of the adapter element 47 for retaining the adapter element 47 in secure engagement with the carrier element 45 as described with reference to the clip 40 of FIGS. 11 to 22.

The Clip 110 like the clip 40 may also be provided as a one-part clip or in two-part form as described with reference to the clip 40. Typically, if the clip 110 is being provided in one-part form, the adapter element 114 would be insert moulded onto the carrier element 112 as already described with reference to the clip 40.

On the other hand, if the clip 110 is being provided in two-part form, the carrier element 112 and the adapter element 114 would be separately manufactured as two individual components and subsequently assembled.

It is envisaged that the clip 110 will be provided with second channels 50 of respective different diameters and/or cross-sections for engaging second members of different diameters and/or different cross-sections to be secured to the first member of the members to be secured together. The formation of the adapter elements 114 with second channels 50 of different diameters and/or cross-sections will be carried out in a similar manner as that already described with reference to the clip 40.

It is envisaged that in the case of the clip 110 where the second channel 50 thereof is to be of maximum transverse cross-sectional diameter, the engagement portion of the adapter element 114 which is formed by the arcuate element 80 and the lead-in forming members 118 will be provided in a similar manner as described with reference to the adapter element 47 of the clip 40.

Otherwise, the clip 110 is similar to the clip 40 and its use is likewise similar.

As described with reference to the clip 40, the clip 110 may also be connected with a plurality of other clips 110 by a tether or a looped tether 41 to form a clip assembly in a similar manner as the clips 40 are connected together by the looped tether 41 to form the clip assembly 42.

A particularly important advantage of the clip 110 is achieved by virtue of the fact that the covering element 115 covers substantially the entire outer surface of the clip 110. In other words, the end panels of the adapter element cover the respective opposite ends of the carrier element, and the side surfaces of the carrier element are completely covered by the side panels of the adapter element. Since the plastics material of the adapter element is of resilience such that it is more deformable than the plastics material of the carrier element, in other words, the force required to deform the plastics material of the adapter element is less than that required to deform the plastics material of the carrier element, and thus the plastics material of the adapter element is more elastic and yielding, and in turn softer than the material of the carrier element, therefore the softer and more yielding material of the adapter element, when the clip is used in conjunction with an endoscope for securing another member, for example, a tubular member to the endoscope, only the surfaces of the clip of the relatively more yielding, elastic and softer material are presented to the subject. In other words, the only surfaces of the clip which come into contact with the inner surfaces and inner linings of a lumen, vessel or cavity in which the endoscope is located or passes through are the relatively yielding, elastic and softer surfaces of the adapter element. The advantage of this is that the adapter element being of a more elastic, yielding softer material than the material of the carrier element, when the outer surfaces of the clip come into contact with the inner surfaces or inner linings of a lumen, vessel or cavity in the body of a subject, there is little or no risk of any grazing, bruising, rupturing, or otherwise injuring or damaging to the inner surface or inner lining of the lumen, vessel or cavity.

It is envisaged, that like the clip 40, the second channel of the clip 110 may be configured to slideably or moveably accommodate the tubular member or other member or instrument, instead of gripping the tubular member or other member or instrument. It is also envisaged that the first channel may be configured to slideably or moveably accommodate the endoscope or other member or instrument in the first channel.

Additionally, like the clip 40, it is also envisaged that an arcuate element similar to the arcuate element 80 may also be located in the first channel or be provided to be inserted into the first channel, for example, to reduce the transverse cross-sectional diameter of the first channel, in which case, the arcuate element for the first channel could be formed integrally with the adapter element, or the arcuate element for the first channel could be provided separately from the adapter element.

It is also envisaged that as with the clip 40, a plurality of arcuate elements could be provided for insertion into the first channel of the clip 110 defining first channels of respective different transverse cross-sectional diameters to accommodate endoscopes or other members or instruments of different transverse cross-sectional diameters. Alternatively, it is envisaged that the adapter element may be configured with an arcuate element configured for locating in the first channel, instead of in the engagement channel, and in which case, the clip would be provided with an arcuate element in the first channel, and no arcuate element in the engagement channel, and the engagement channel would form the second channel.

However, as discussed above both with reference to the clip 40 and the clip 110, the clip 110 may be provided with two arcuate elements, one in the first channel and one in the engagement channel. In which case, the two arcuate element could be integrally formed with the adapter element, or the adapter element may be provided with one arcuate element only, for example, for the engagement channel or the first channel, and a separate arcuate element could be provided for the other one of the first channel and the engagement channel.

Referring now to FIGS. 37 to 40, there is illustrated a clip according to another embodiment of the invention indicated generally by the reference numeral 130. The clip 130 is somewhat similar to the clip 7 described with reference to FIGS. 1 to 10, and where appropriate similar components are identified by the same reference numerals. The clip 130 is also suitable for releasably securing first and second elongated members together, for example, the clip 130 is suitable for securing a second member, such as a tubular member 5 to an endoscope 3 as already described with reference to the clip 7 of FIGS. 1 to 10. In this embodiment of the invention the clip 130 is formed of a resilient plastics material and is formed in one piece by, for example, injection moulding.

The clip 130 comprises a body member 132. A pair of first side members 134 extend from one side 135 of the body member 132 and define the first channel 17. The first side members 134 are similar to the first side members 14 of the clip 7. The first side members are resilient and are deformable outwardly in the direction of the arrows A for accommodating the first member, for example, the endoscope 3 into the first channel 17 defined by the first side members 134.

A pair of second side members 137 extend from the opposite side 138 of the body member 132 at spaced apart locations 139, and extend to longitudinally extending distal side edges 140 along which the second side members 137 join to form a passageway 145 in the form of an elongated engagement bore 147 for accommodating the second elongated member, for example, a tubular member therethrough, for in turn securing the tubular member to the endoscope or other such instrument engaged in the first channel 17. The second side members 137 extend from the body member 132 in the opposite direction to that from which the first side members 134 extend from the body member 132.

The first channel 17 defined by the first side members 134 defines a first central axis 149. The engagement bore 147 defined by the second side members 137 defines a second central axis 150 which extends parallel to the first central axis 149, so that the endoscope or other such instrument in the first channel 17 and the tubular member or other instrument in the engagement bore 147 extend parallel to each other. In this embodiment of the invention the first side members 134 resiliently grip the endoscope or other instrument in the first channel 17, while the engagement bore 147 in this embodiment of the invention is configured to slideably engage the tubular member or other instrument extending therethrough.

A pair of spaced apart tether accommodating apertures, which in this embodiment of the invention are formed by a pair of elongated spaced apart tether accommodating bores 152 extend parallel to each other through the body member 132 for accommodating respective legs of a looped tether, for example, the looped tether 9 of the clip 7 described with reference to FIGS. 1 to 10.

In this embodiment of the invention the first side members define the first channel 17 of partly circular transverse cross-section, and the first channel 17 extends around the first central axis 149 between the first distal side edges 25 thereof through an angle α of approximately 290° in the relaxed non-deformed state of the first side members 134. When an endoscope 3 is engaged in the first channel 17, the first side members 134 are deformed outwardly in the direction of the arrows A, and extend around the endoscope an angular distance of approximately 220°. This deforming of the first side members 134 outwardly in the direction of the arrows A in order to engage an endoscope or other such instrument results in the first side members 134 being resiliently biased inwardly into engagement with the endoscope or other such instrument towards their natural relaxed non-deformed state for tightly and securely gripping the endoscope therebetween.

In use, the clips 130 may be used individually or may be connected together in series in the form of a clip assembly, similar to the clip assembly 10 of the clips 7 described with reference to FIGS. 1 to 10. When provided as a clip assembly, the clips 130 would be sequentially secured to the endoscope 3 or other such instrument at spaced apart intervals along the endoscope 3 by engaging the endoscope 3 or other such instrument in the first channel 17. The tubular member or other instrument would then be slidably entered into the engagement bores 147 of the clips 130 spaced apart along the endoscope or other such instrument.

Otherwise, the clip 130 according to this embodiment of the invention and its use is similar to that of the clip 7 described with reference to FIGS. 1 to 10.

While the carrier elements and the adapter elements of the clips 40 and 110 have been described as comprising specific materials, it will be readily apparent to those skilled in the art that the carrier elements and the adapter elements may be of any other suitable material. It is envisaged that the carrier elements 45 and 112 of the embodiments of the clip described with reference to FIGS. 11 to 22 and FIGS. 23 to 35 may be of any other material other than a plastics material, and may be of a rigid material, for example, a metal material.

While a pair of tether accommodating bores have been described in each clip for accommodating the two legs of the looped tether, in some embodiments of the invention it is envisaged that a single tether accommodating bore or other suitable tether accommodating aperture may be provided in each clip for accommodating a single tether along which the clips would be located in series, and the respective opposite ends of the tether could be secured to the distal most clips at the respective opposite ends of the tether, or other suitable stop means could be provided at the distal most ends of the tether for preventing the clips becoming detached from the tether. It is also envisaged that the tether accommodating bore or bores, as the case may be, of each clip may be provided in any suitable location of the clips other than the locations described. Indeed, it is envisaged in some embodiments of the invention that the bore or bores, as the case may be, may be provided externally of the clips, for example, on an external surface of the clips.

While the clips and the clip assemblies have been described for securing a tubular member to an endoscope, the clips may be provided for securing any member to an endoscope or to any other member. Needless to say, the clips according to the invention may be provided for securing any two members together to form an assembly of the two members and the clip or clip assembly, and while the clip and the clip assembly have been described as securing a tubular member to an endoscope in the form of an instrument assembly, the clip or the clip assembly may be provided to secure any type of members together to form an assembly of those two members and the clip or the clip assembly.

It is also envisaged that while the first and second channels have been described as being elongated channels, while this is desirable it is not essential. In some embodiments of the invention the first and second channels may be relatively short.

While the embodiments of the clips described have been described as comprising the first and second channels extending parallel to each other, in some embodiments of the invention it is envisaged that the first and second channels may extend at an angle greater than zero relative to each other, for example, it is envisaged that the channels may extend at 45° to each other, at 90° to each other, or at any desired angle to each other.

While the first and second channels and the engagement channels and the engagement bore have been described as being of partly circular transverse cross-section, it is envisaged that the first, second and engagement channels may be of any other suitable or desired transverse cross-section, for example, square, hexagonal, octagonal or any other desirable polygonal transverse cross-section. Indeed, it is envisaged that the transverse cross-section of the first and second channels, the engagement bore and possibly the engagement channel also, would typically, be matched to the transverse cross-section of the first and second members, as the case may be, to be engaged in the respective channels or bore.

It will of course be appreciated that while the first and second and engagement channels and the engagement bore have been described as being of specific transverse cross-sectional diameters, the first, second and engagement channels and the engagement bore may be of any suitable diameter or of any other suitable transverse cross-section.

It is also envisaged that the clip 130 described with reference to FIGS. 37 to 40 may be provided in the form of a two part clip comprising a carrier element and an adapter element. In which case, it is envisaged that the carrier element may be similar to the carrier element of either of the clips described with reference to FIG. 11 to 22 or 23 to 36, or alternatively, the carrier element may be provided with the engagement members forming a first passageway in the form of a bore instead of in the form of a channel. In cases where the carrier element is similar to the carrier element of the clip of FIG. 11 to 22 or the carrier element of the clip described with reference to FIGS. 23 to 36, it is envisaged that the adapter element would be provided with an engagement portion which would define a second passageway in the form of an engagement bore similar to the engagement bore 147 of the clip 130, and the engagement portion forming the engagement bore 147 would be engageable in the engagement channel of the carrier element. On the other hand, if the engagement members of the carrier element were configured to define the first passageway in the form of an elongated bore instead of an engagement channel, it is envisaged that the adapter element would be provided in two halves which would engage the carrier element from the respective opposite ends thereof.

In the embodiments of the invention where the clip 130 is formed in two parts with a carrier element and an adapter element, it is envisaged that the adapter element will be of a more yielding, elastic and softer material than the material of the carrier element, in order to avoid grazing, bruising, rupturing or otherwise injuring or damaging the inner surface or the inner lining of lumens, vessels or cavities through which the clip, when attached to an endoscope or other surgical instrument is being urged. Additionally, it is envisaged that the material of the adapter element will be of a resilience such that the force or pressure required to deform the material will be less than the force or pressure required to deform the material of the carrier element.

The invention claimed is:

1. A clip assembly for releasably securing a pair of elongated members together, the clip assembly comprising:

a plurality of the clips, each clip comprising:

a body member, a pair of spaced apart first side members extending from the body member, the first side members defining a first channel and cooperating with each other for releasably gripping and retaining a first one of the members to be secured together in the first channel, a pair of second side members extending from the body member, the second side members defining a passageway for accommodating a second one of the members to be secured together therein, and a pair of spaced apart tether accommodating apertures in or on the body member, defining respective tether central axes extending parallel to each other, and a tether in the form of an endless loop, one leg of the loop passing through one of the tether accommodating apertures of the respective clips and the other leg of the loop passing through the other one of the tether accommodating apertures of the respective clips, with the clips retained in series by the tether.

2. A clip assembly as claimed in claim 1 in which the second side members of each clip extend from the body member from a side opposite to a side of the body member from which the first side members extend, the first side members terminating in respective spaced apart first distal side edges defining a first open mouth to the first channel, the second side members terminating in respective spaced apart second distal side edges to form the passageway as a second channel defining a second open mouth to the second channel, the first and second open mouths facing away from the first and second channels in opposite directions.

3. An assembly comprising an elongated first member and an elongated second member releasably secured together by the clip assembly as claimed in claim 1, the clips of the clip assembly being spaced apart longitudinally along the first and second members, one of the first and second members comprising an endoscope, and the other one of the first and second members comprising a tubular member or an instrument.

4. A clip assembly as claimed in claim 1 in which the first channel of each clip defines a longitudinally extending first central axis, and the passageway of each clip defines a longitudinally extending second central axis extending parallel to the first central axis thereof.

5. A clip assembly as claimed in claim 4 in which the tether central axes of each clip extend substantially parallel to the first central axis defined by the first channel.

6. A clip for securing a pair of members together, the clip comprising:

a carrier element defining a first channel for engaging a first one of the pair of the members to be secured together, and a first passageway of a first transverse cross-section for accommodating an adapter element therein defining a second passageway therethrough of a second transverse cross-section less than the first transverse cross-section of the first passageway for engaging a second one of the pair of the members to be secured together, and a covering element configured for covering at least a portion of an external surface of the carrier element.

7. A clip for securing a pair of members together, the clip comprising:

a carrier element defining a first channel for engaging a first one of the pair of the members to be secured together, and a first passageway defining a first transverse cross-section, an adapter element comprising an engagement portion engageable in the first passageway and defining a second passageway extending therethrough of a second transverse cross-section less than the first transverse cross-section of the first passageway for engaging a second one of the pair of the members to be secured together, and a covering element extending from the engagement portion of the adapter element configured for covering at least a portion of an external surface of the carrier element.

8. A clip as claimed in claim 7 in which the carrier element comprises a body member, and the first channel is defined by a pair of spaced apart first side members extending from the body member, and the first passageway is defined by a pair of spaced apart engagement side members extending from the body member, the engagement side members and the first side members extend from the body member in respective opposite directions therefrom.

9. A clip as claimed in claim 8 in which the body member, the first side members and the engagement side members of the carrier member are integrally formed in one piece.

10. A clip as claimed in claim 8 in which the covering element comprises end covering members extending from the engagement portion of the adapter element adjacent respective opposite ends thereof for covering respective opposite ends of the carrier element.

11. A clip as claimed in claim 10 in which the end covering members extend from the engagement portion of the adapter element from the respective opposite ends thereof to locations adjacent first distal side edges in which the first side members of the carrier element terminate.

12. A clip as claimed in claim 8 in which the engagement side members terminate in respective distal side edges spaced apart from each other, the distal side edges defining an open mouth to the first passageway for accommodating the adapter element into the first passageway.

13. A clip as claimed in claim 7 in which the first channel defines a longitudinally extending first central axis, and the first passageway defines a longitudinally extending first passageway central axis extending substantially parallel to the first central axis.

14. A clip as claimed in claim 13 in which at least one tether accommodating aperture is provided in or adjacent the carrier element for accommodating a tether therethrough, the tether accommodating aperture defining a longitudinally extending tether central axis extending substantially parallel to the first central axis.

15. A clip assembly comprising a plurality of the clips as claimed in claim 14 retained in series by a tether.

16. A clip as claimed in claim 7 in which a securing means is provided for securing the covering element to the carrier element.

17. A method for producing the clip as claimed in claim 7 in which the method comprises forming the carrier element and forming the adapter element and assembling the adapter element to the carrier element.

18. A method for producing the clip as claimed in claim 7, the method comprising forming one of the carrier element and the adapter element, and placing the formed one of the carrier element and the adapter element in a mould cavity of an insert moulding die and forming the other one of the carrier element and the adapter element in the mould cavity of the insert moulding die by insert moulding.

19. A clip as claimed in claim 7 in which the engagement portion of the adapter element comprises an arcuate element having an inner surface defining the second passageway as a second channel for engaging the second member, and an outer surface defining the first passageway and being engageable in the first passageway.

20. A clip as claimed in claim 19 in which the arcuate element of the adapter element terminates in a pair of spaced apart opposite longitudinally extending second distal side edges defining an elongated second open mouth to the second channel for accommodating the second member therethrough.

* * * * *